US011285321B2

(12) United States Patent
Ganguly et al.

(10) Patent No.: US 11,285,321 B2
(45) Date of Patent: Mar. 29, 2022

(54) METHODS AND APPARATUSES FOR IMPROVING PERIPHERAL NERVE FUNCTION

(71) Applicants: The Regents of the University of California, Oakland, CA (US); U.S. Government Represented by the Department of Veterans Affairs, Washington, DC (US); LightSide MD, LLC, Los Altos, CA (US)

(72) Inventors: Karunesh Ganguly, San Francisco, CA (US); Adelyn Tsu, San Francisco, CA (US); Nikhilesh Natraj, San Francisco, CA (US); Gabriel Philip Howles-Banerji, Oakland, CA (US); Rajiv Doshi, Los Altos, CA (US); Kondapavulur T. Venkateswara-Rao, San Jose, CA (US)

(73) Assignees: The Regents of the University of California, Oakland, CA (US); U.S. Government Represented by the Department of Veterans Affairs, Washington, DC (US); LightSide MD, LLC, Los Altos, CA (US)

( * ) Notice: Subject to any disclaimer, the term of this patent is extended or adjusted under 35 U.S.C. 154(b) by 65 days.

(21) Appl. No.: 16/461,085

(22) PCT Filed: Nov. 14, 2017

(86) PCT No.: PCT/US2017/061507
§ 371 (c)(1),
(2) Date: May 15, 2019

(87) PCT Pub. No.: WO2018/093765
PCT Pub. Date: May 24, 2018

(65) Prior Publication Data
US 2020/0061378 A1 Feb. 27, 2020

Related U.S. Application Data

(60) Provisional application No. 62/422,432, filed on Nov. 15, 2016.

(51) Int. Cl.
*A61N 1/00* (2006.01)
*A61N 1/36* (2006.01)
(Continued)

(52) U.S. Cl.
CPC .......... *A61N 1/36031* (2017.08); *A61B 5/002* (2013.01); *A61B 5/30* (2021.01);
(Continued)

(58) Field of Classification Search
CPC .......... A61B 5/30; A61B 5/0476; A61B 5/048; A61B 5/0482; A61B 5/375; A61B 5/002;
(Continued)

(56) References Cited

U.S. PATENT DOCUMENTS 5,871,534 A 2/1999 Messick et al.
8,165,685 B1 4/2012 Knutson et al.
(Continued)

FOREIGN PATENT DOCUMENTS

| CN | 101232860 A | 7/2008 |
| CN | 103608069 A | 2/2014 |
| CN | 104902806 A | 9/2015 |

*Primary Examiner* — Scott M. Getzow
(74) *Attorney, Agent, or Firm* — Shay Glenn LLP

(57) ABSTRACT

Methods and apparatuses for sensory electrical stimulation of the peripheral nervous system to improve human motor function and performance are described. Methods and devices may be used to enhance physical performance of athletes, professionals, and gamers or improve motor function (hand, finger and limb movement) in patients rehabili- (Continued)

tating from neurological deficits and impairments caused by stroke, traumatic brain injury and other neurologic or non-neurologic conditions. These apparatuses and methods may be used for physical training and mental training (to improve memory and functional performance including motor coordination, limb-eye coordination, occupational and recreational skills) through periodic or sustained sensory electrical stimulation. Treatment plans may be based on biomarkers and may be used alone or in combination with other apparatuses. Learning and feedback techniques individualize treatment parameters depending on the subject's neurologic and motor function in diseased patients and healthy users.

7 Claims, 20 Drawing Sheets

(51) Int. Cl.
*A61B 5/00* (2006.01)
*A61N 1/04* (2006.01)
*A61B 5/30* (2021.01)
*A61B 5/375* (2021.01)
*A61N 1/378* (2006.01)

(52) U.S. Cl.
CPC ............ *A61B 5/375* (2021.01); *A61B 5/4047* (2013.01); *A61B 5/4824* (2013.01); *A61B 5/4848* (2013.01); *A61B 5/7275* (2013.01); *A61B 5/7455* (2013.01); *A61N 1/0456* (2013.01); *A61N 1/36034* (2017.08); *A61B 2505/09* (2013.01); *A61N 1/0484* (2013.01); *A61N 1/0492* (2013.01); *A61N 1/36021* (2013.01); *A61N 1/378* (2013.01)

(58) Field of Classification Search
CPC ... A61B 5/4047; A61B 5/4824; A61B 5/4848; A61B 5/7275; A61B 5/7455; A61B 2505/09; A61B 5/374; A61N 1/36031; A61N 1/36014; A61N 1/0472; A61N 1/36034; A61N 1/0456; A61N 1/0484; A61N 1/0492; A61N 1/36021; A61N 1/378; Y02A 90/10; G16H 50/30
See application file for complete search history.

(56) References Cited

U.S. PATENT DOCUMENTS

| | | |
|---|---|---|
| 2008/0319505 A1 | 12/2008 | Boyden et al. |
| 2009/0094305 A1 | 4/2009 | Johnson |
| 2010/0113150 A1 | 5/2010 | Chan et al. |
| 2014/0194948 A1 | 7/2014 | Strother et al. |
| 2014/0200432 A1* | 7/2014 | Banerji ................. G16H 20/70 600/383 |
| 2014/0330394 A1 | 11/2014 | Leuthardt et al. |
| 2015/0065838 A1 | 3/2015 | Wingeier et al. |
| 2015/0066104 A1* | 3/2015 | Wingeier ............. A61B 5/4836 607/45 |
| 2015/0081057 A1 | 3/2015 | Hamada et al. |
| 2015/0094785 A1 | 4/2015 | Kilgard et al. |
| 2015/0142082 A1 | 5/2015 | Simon et al. |
| 2015/0290457 A1 | 10/2015 | Palermo et al. |
| 2015/0321000 A1* | 11/2015 | Rosenbluth ........ A61N 1/36034 607/48 |
| 2019/0380625 A1* | 12/2019 | Lindberg ............. A61B 5/1126 |

* cited by examiner

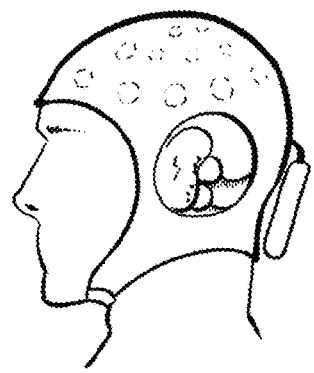
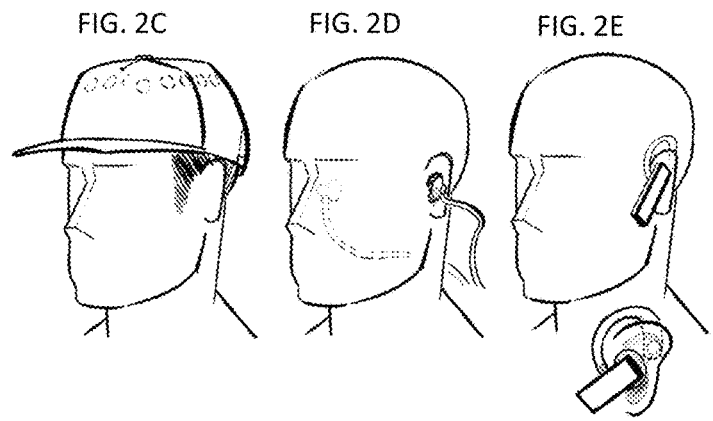
FIG. 2A
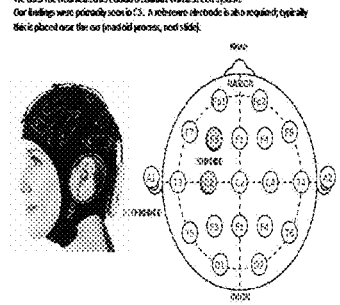
EEG locations: Any two or more locations may be chosen.
FIG. 2B
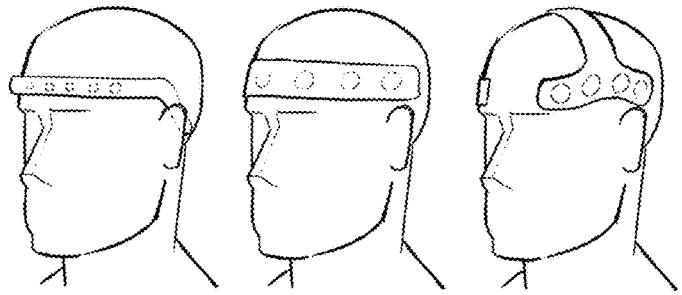
FIG. 2F  FIG. 2G  FIG. 2H

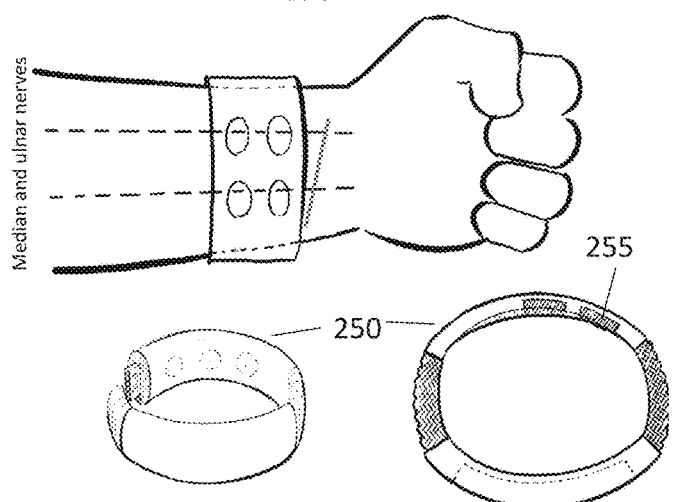
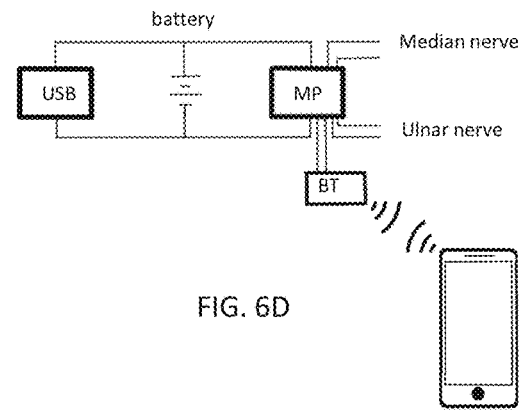
FIG. 6A
FIG. 6B
FIG. 6C
FIG. 6D
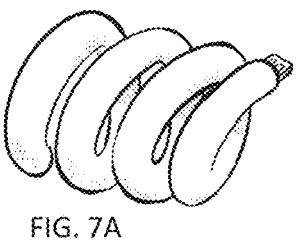
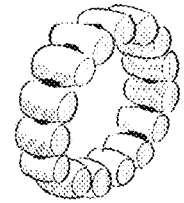
FIG. 7A
FIG. 7B FIG. 8A
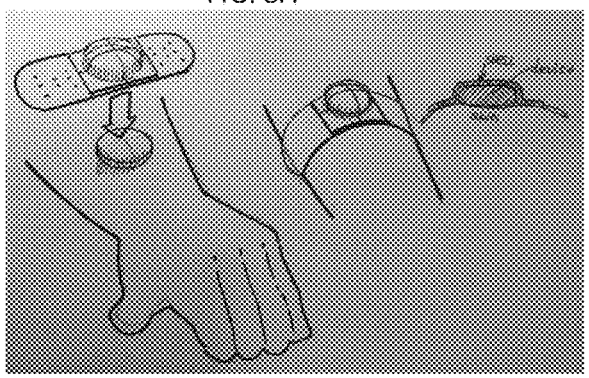
FIG. 8B
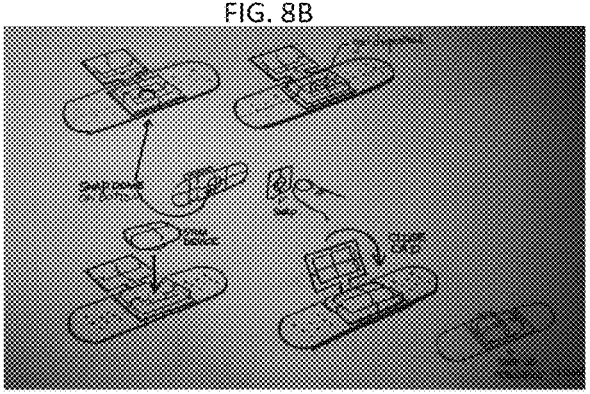
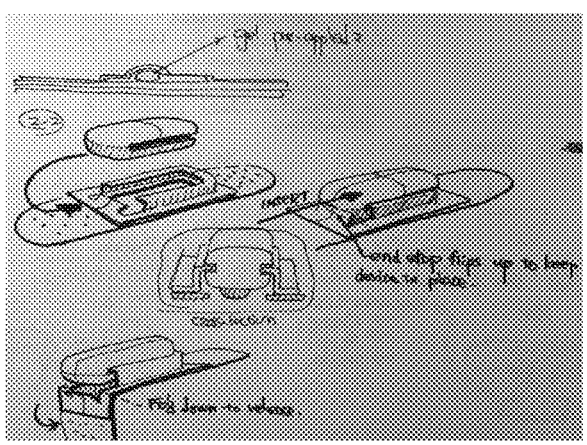
FIG. 8C
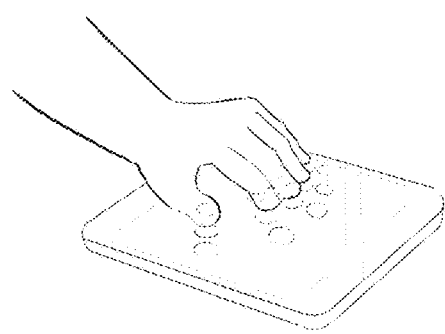
FIG. 9

FIG. 10

| Condition | Nerve | Measurements |
|---|---|---|
| Stroke/traumatic brain injury/or other acquired brain injury with speech, language, dysphagia, upper-limb and lower-limb deficits | Upper Limb (sensory and motor nerves C3-T2; including ulnar, median, radial, axillary, cutaneous of the entire arm, lateral cutaneous nerve of forearm, brachial cutaneous nerves)<br><br>Lower Limb (e.g. S1-S5; L1-5; branches of sciatic such as tibial and peroneal, femoral, obturator; saphenous; foot cutaneous nerves; plantar surface)<br><br>Oromotor (CN 3-12; pharyngeal nerves, cutaneous nerves in mouth)<br><br>Importantly, we may also use any combination of the nerves listed above (e.g. median, ulnar, radial nerves at the same time) | • Upper limb<br>   o Finger kinematics<br>   o Hand open/close<br>   o Tapping<br>   o Interactions with game/phone<br>• Lower Limb<br>   o Bracelet at ankle that can monitor step length, stride, gait speed, stance<br>   o Motion capture of speed<br>   o Use of camera to measure speed<br>• Speech/Dysphagia<br>   o Subjective sxs<br>   o Recording of speech (either spontaneous or reading text)<br>   o Swallow test at home |
| Gait disturbances, including age related decline in gait parameters; sensory neuropathy, gait ataxia from cerebellar and neuropathy, Parkinsonism, small-vessel ischemic disease | Girdle for gluteus minimus; Leg/thigh sleeves for lower extremity | • Place cell phone in a pocket on girdle (likely horizontal in the midline) and using analysis of phones integrated motion sensors to analyze gait and provide feedback<br>• Place motion sensors in critical locations along the lower extremities using adhesives or integrated into girdle/sleeves<br>• Motion capture (using e.g., Microsoft Kinect) |
| Parkinson's disease | Large and small muscles, particularly large muscles | • Use of motion capture or motion sensors to look at gait, but may be complex for a home-based system<br>• Simple tracking of smoothness and responsiveness of finger motion as patient traces finger on a tablet may be a good biomarker of overall response.<br>• Simple game could be chasing a character running through a maze on the screen. The speed and complexity of the maze could be modulated and titrated to the patient's ability and response to PNS. |

FIG. 11

| Condition | Area | Intervention |
|---|---|---|
| Essential tremor | wrist | • Haptic glove<br>• Mobile phone using motion sensors within the phone to detect tremor and sound/vibration of the phone as sensory feedback to patient |
| Senile loss of proprioception or decreased ability to respond to imbalance | Large and small muscles | • Balance training and balance recovery to decrease falls (number 1 cause of accidents in people over 65)<br>• Similar considerations as for Parkinson's Disease<br>• Use of a sensored mat to follow gait parameters<br>• Use of cell phone in pocket to measure gait parameters (e.g. stumbles) during regular walking or standing or standing with eyes closed |
| Upper motor neuron degenerative disease like primary lateral sclerosis, ALS, Multiple Sclerosis, spinal cord injury | • Same nerves in upper and lower extremity as in stroke | • Subjective measures of spasticity; speed of movements in upper and lower extremity<br>• Accelerometers to detect changes in function |
| Post-polio syndrome, and other lower motor neuron diseases such as ALS | Lower and upper extremity electrodes targeted to specific affect limb/limb; specific targets are similar to stroke | • Self report of fatigue pain<br>• Force transducer linked to phone to measure force and muscle strength |
| Cerebral Palsy | Fine motor and large muscle electrodes; Also regions identified for stroke in upper and lower extremity; Pharyngeal nerves for dysphagia | • Identical to stroke |
| Neurological Movement Disorders (Tics, Chorea, Hemiballimus, Ataxia, Rigidity) | Fine motor and large muscle electrodes; Also regions identified for stroke in upper and lower extremity; Pharyngeal nerves for dysphagia | • Subjective assessment of movements<br>• Follow frequency of movements using an accelerometer |
| Restless Leg Syndrome; Periodic Limb Movements; Periodic Limb Movements of Sleep | Lower extremity muscles and sensory/motor nerves; e.g. S1-S5, L1-5; branches of sciatic, femoral, obturator, saphenous | • Subjective reporting<br>• Stimulation has a sensor to monitor. This might be an accelerometer, gyroscope or EMG electrode. |

FIG. 12

| Condition | Target | Feedback |
|---|---|---|
| Cramps | Lower extremity muscles and sensory/motor nerves e.g. S1-S5; L1-5; branches of sciatic, femoral, obturator; saphenous; Similar in the upper extremity | • Subjective reporting<br>• Stimulation has a sensor to monitor. This might be an accelerometer, gyroscope or EMG electrode. |
| Trigeminal neuralgia | Adhesive facial electrode targeting CN5, 7 and associated sensory nerves; | • Self-reported symptoms |
| Migraine | Adhesive facial electrode targeting CN5, 7 and associated sensory nerves; Occipital nerve; Auricular nerve | • Titration based on self-reported symptoms of headache duration, frequency, severity |
| Chronic hiccups or Diaphragmatic paralysis | Sensory reference to diaphragm is the shoulder; maybe able to use cutaneous shoulder electrode | • Titration based on self-report<br>• Accelerometer/force transducer on the stimulation electrode to detect chest wall movements |
| Chronic vertigo | Adhesive facial electrode targeting CN5, 7 and associated sensory nerves; Occipital nerve; Auricular nerve | • Self-reported frequency of symptoms |
| Reflex sympathetic dystrophy | Wrist: Sleeve device or band | • Feedback: LED and sensor to measure blood flow (like pulse ox), Pain biofeedback app |
| Bell's Palsy, Facial Spasm, Blepharospasm | Adhesive facial electrode | • Subject response<br>• Video of the facial movements; with automatic measurement of changes in function based on motion detection algorithms<br>• Strain gauge and/or accelerometer on the electrode to detect movement |
| Chronic nausea | | • Training: VR game to simulate motion |

FIG. 13

| Condition | Target | Intervention |
|---|---|---|
| Dysphagia | Trigeminal, pharyngeal surface; upper esophageal, vagus nerves | • Self-report of symptoms<br>• Could be tied to EMR and thus objective tests of dysphagia (e.g. fluoroscopy, bed-side swallow test) |
| Torticollis | Sternocleidomastoid; CN5, 7 and associated sensory nerves; Occipital nerve; Auricular nerve | • Self report of reduced tone, dystonic posture and improved volitional control of muscle<br>• Accelerometer in stimulation electrode to measure tremor or dystonic tone<br>• EMG recordings in the stimulation recording to measure abnormal co-contraction of muscles |
| Impotence (Non-vascular causes, i.e., not due to atherosclerosis) | Perineum (pudendal nerve); Subsensory stimulation may be ideal | • Feedback: LED and sensor to measure blood flow (like pulse oximeter) or stretch sensor to measure elongation. Adhesive sensor |
| Premature ejaculation | Cutaneous inputs to S1-S5; perineal nerves<br>Pudendal nerve and branches | • Subjective report of symptoms |
| Pelvic floor dysfunction | Perineum adhesive electrode, subsensory stimulation | • Improve awareness, muscle control, strength training |
| Urinary Incontinence; spastic bladder; Overactive bladder | Cutaneous inputs to S1-S5; perineal nerves<br>Pudendal nerve and branches | • Reduce spasticity, improve bladder tone; reduce associated symptoms |
| Insomnia and other disorders of sleep wake cycles | Adhesive facial electrode targeting CN5, 7 and associated sensory nerves; Occipital nerve; Auricular nerve; Also upper and lower limb targets as identified for stroke; Stimulation may be tailored to sleep cycles | • Self report<br>• Accelerometer in stimulation device to measure stages of sleep<br>• EMG to detect movements<br>• EEG to detect sleep waves<br>• EOG to measure eye movements |
| Low-Back Pain including Sciatica, lumbar radiculopathy; peripheral neuropathy | Upper and lower limb targets as identified for stroke | • Self-report of symptoms on the app |
| Gastroparesis | Cranial nerves 10, 1, 12 | |
| Obstructive sleep apnea/snoring | Hypoglossal | Objective or subjective assessment of snoring, sleepiness |

FIG. 14

| User | Sensors | Improvements |
|---|---|---|
| Professional athletes | Large muscles; place electrodes in stretchy washable sleeves for leg or arm with removable sensors/electrodes; could also involve stimulation of single and multiple nerves as outlined in "STROKE" section in the table above. | Training:<br>• Stationary bike: easy to monitor feedback and dynamically control resistance.<br>• Hand bike for arms<br>• Motion capture<br>• More simplistically can use weight machines – software will provide targets and trainer manually inputs results.<br>Feedback: visual, sound, haptic<br>• Upper extremity: Throwing athletes (Quarterbacks, Pitchers), Fencing, Tennis, swimming<br>• Lower extremity: Track and field, NFL, basically anything |
| Dancers | Similar electrodes as athletes except we may also stimulate nerves that are described in the STROKE LOWER LIMB section. | Training/feedback as above, perhaps greater role for motion capture |
| Musicians (Drummers, string instruments, woodwinds, Pianists) | Wrist system; we may also use upper limb sensory/motor nerve combinations as outlined in the STROKE section | Feedback/training system:<br>• System may not necessarily relate directly to the patient's musical discipline. Touch screen based speed, dexterity, and individuation game may be ample.<br>• More elaborately, tablet analyzes performed music (ipad displays music exercises and analyzes performance)<br>• Electronic drum kit, electronic keyboard, etc. |
| Physicians (Surgeons, interventional radiologists, cardiologists) | Wrist system; we may also use upper limb sensory/motor nerve combinations as outlined in the STROKE section | Feedback/training<br>• Dexterity and individuation<br>• Reaction time and learning of complex sequences<br>• Training of VR system that mimics endoscopic or other remote operation systems |
| Videogamers | Wrist system; we may also use upper limb sensory/motor nerve combinations as outlined in the STROKE section | • Stimulate while doing other things (sleep, surfing internet, watching TV, etc)<br>• Subsensory or barely sensory stimulation<br>• Feedback/Training: Adjust to their game of choice; Touch based training game on tablet or phone<br>• Use of accelerometer in system to detect spontaneous changes (i.e. not task-related) |
| People who type (transcriptionists, stenographers) | Wrist system; we may also use upper limb sensory/motor nerve combinations as outlined in the STROKE section | Similar to video gamers |

FIG. 15A

| Stimulation parameters | General range | Preferred ranges for SES |
|---|---|---|
| Pulse duration | 0.01 – 1 second | 0.125-1 milliseconds |
| Duty Cycle | 10s-on + 10s-off cycle | 1%-99%, values closer to 50% will be preferred |
| Shape/waveform | Biphasic, Square wave, sinusoidal, sawtooth, triangular | Biphasic pulses are preferred; but non-charge balanced square waves and other waves ma be used |
| Pulse frequency | 0.1-100 Hz; continuous stimulation or | 1-10Hz, delivered in 1-Hz pulse trains (5 pulses/train) |
| Intensity of stimulation | Range: mild (tingling) to strong paresthesias. Depends on sensation level (function of skin conductivity, location and size of electrode) | Subsensory- current intensity (mA) just below sensory threshold; below pain threshold; below visible muscle/motor contraction |
| Duration of treatment | 20-120 minutes, 1-5 times/day<br><br>2-7 sessions/week<br><br>Total time: 1 day to 1 year | 10-20 minutes per session<br><br>2-3 times per week<br><br>Total time: 1 week-1 month |

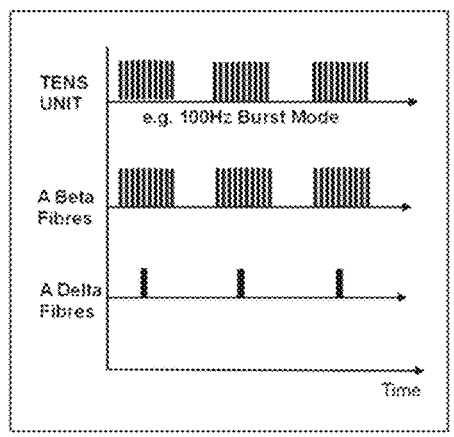

FIG. 15D

Outcome measures
Body/structure function
    Spasticity (is a muscle control disorder that is characterized by tight or stiff muscles and an inability to control those muscles); measured using
        Using EMG
        Wrist and finger velocity
        Hand and finger tapping frequency
        Clinical tools
    Force
        UE force
        LE force
    Gait velocity
        10-m gait velocity test
        10-min walk, 6-minute walk
        Timed Up and Go test
        Jebsen-Taylor Hand Function Test

FIG. 16

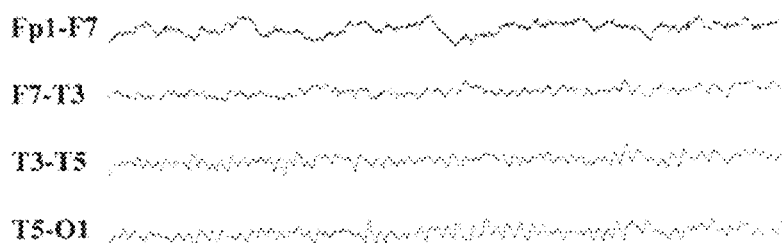
FIG. 17
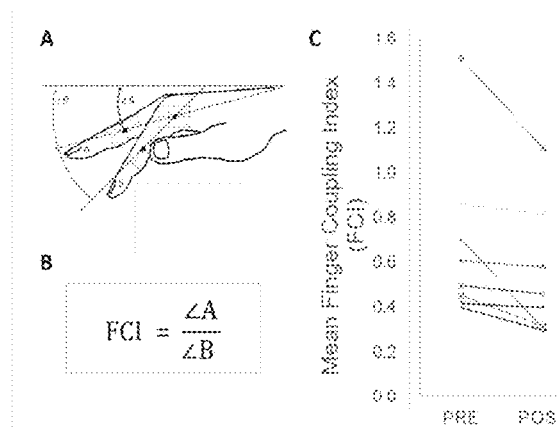
FIG. 18
FIG. 19

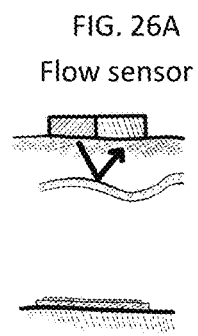
FIG. 25A
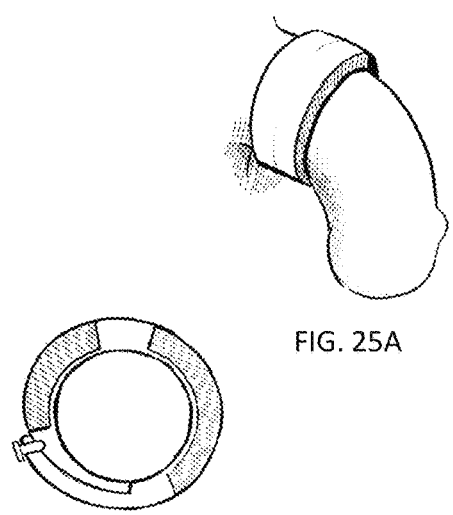
FIG. 25B
FIG. 26A
Flow sensor
FIG. 26B
Stretch sensor
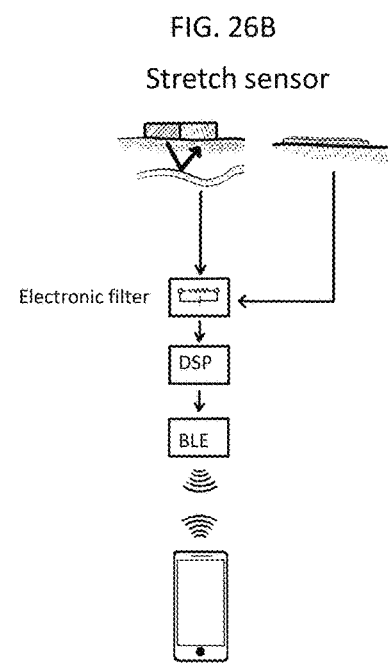

METHODS AND APPARATUSES FOR IMPROVING PERIPHERAL NERVE FUNCTION

CROSS REFERENCE TO RELATED APPLICATIONS

This application claims priority to International PCT Application No. PCT/US17/61507, filed on Nov. 14, 2017, which claims priority to U.S. Provisional Patent Application 62/422,432, filed Nov. 15, 2016 and entitled "Methods and Apparatuses for Improving Peripheral Nerve Function," which is hereby incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Methods and apparatuses (including devices, algorithms and systems) for electrical stimulation of peripheral nerves to improve peripheral nerve function are described and illustrated herein. These methods and apparatuses may be configured to modify cortical control in the brain, which may enhance peripheral nerve function and thereby.

BACKGROUND

Peripheral nerve stimulation (PNS) has the potential to treat chronic neurological diseases or conditions. Somatosensory electrical stimulation (SES) is a form of PNS that involves modulation of sensory nerves. SES has shown promise in helping to modulate motor function. However, it has not been adopted into clinical practice because of great variability in clinical efficacy.

Stroke represents a very common neurological condition. Motor disability after stroke is primarily due to impaired hand or leg function and the loss of finger dexterity and movement/mobility. The annual incidence of stroke in the US is approximately 700,000, with half of stroke survivors experiencing long-term motor disability. While current rehabilitation approaches have helped individuals regain function, a substantial number of patients continue to experience chronic upper and/or lower limb dysfunction and disability after stroke. Impaired hand and finger function are particularly important contributors to such disability. Human hand function is required to complete activities of daily living; it is also required for occupational skills and for societal integration.

There is a need in the art for new approaches to restore hand and finger dexterity and to reduce disability after stroke.

SUMMARY OF THE DISCLOSURE

In general, described herein are methods and apparatuses (including devices, algorithms and systems) for sensory electrical stimulation of the peripheral nervous system to improve peripheral nerve function, such as motor function and performance. These methods typically include stimulation of one or more nerves in a manner that is non-irritating, and may be barely detectable or undetectable to the subject receiving the electrical stimulation; this stimulation may be adjusted by the user and/or may be continuously or iteratively adjusted via feedback based on a measure or indicator of subject performance when using the stimulated peripheral nerve and/or an indicator such as a biomarker including electroencephalogram (EEG) data. In any of these methods and apparatuses, a training task may be included (e.g., a game, videogame, manual dexterity game, etc.) and the training task may be performed during or after (e.g., immediately after, or within less than 5 min, 10 min, 15 min, 20 min, 25 min, 30 min, 35 min, 40 min 45 min, 50 min, 55 min, 60 min, (e.g., 30 minutes) from) the stimulation period. For example, described herein are apparatuses (e.g., devices, systems, etc.) for improving a subject's peripheral nerve function by closed-loop control of applied stimulation.

For example, an apparatus may include: a first input comprising one or more of: a biomarker monitor and a performance indicator input; a stimulator having one or more electrodes, a power source, a controller functionally coupled to the first input, wherein the controller is configured to apply an electrical stimulation to a peripheral nerve and to measure at least one of: a biomarker or a performance indicator from a task that activates the peripheral nerve to which the electrical stimulation was applied; wherein the stimulator is configured to iteratively apply electrical stimulation and adjust the electrical stimulation based on one or more of: the measured biomarker and the performance indicator.

As will be described herein, a biomarker monitor may generally include any sensor or combination of sensors configured to detect a biological marker from the subject. For example, a biomarker monitor may include one or more electrodes for detecting biopotentials, e.g., electromyogram (EMG), electroocculogram (EOG), electroencephalogram (EEG), etc. For example, any of these apparatuses may include one or more electrical sensors (e.g., EMG sensors, etc.) as part of a biomarker monitor. The biomarker monitor may be separate from the stimulator, or it may be coupled or combined with the stimulator. For example, the same electrodes applying electrical stimulation may be used to detect/sense electrical activity in the subject, including in the subject's peripheral nerve(s). The biomarker monitor may comprise an electroencephalogram (EEG) sensor or an electromyogram (EMG) sensor (or both). The controller (and/or the biomarker monitor) may be configured to measure the change in EEG/power spectral density or spike-field coherence in a motor cortex of a brain. The controller (and/or the biomarker monitor) may be configured to measure a change in delta or theta wave portion of an EEG.

A performance indicator input may be any appropriate performance indicator input, and may be configured to receive input from (or may include as part of the performance indicator input) any apparatus that detects patient performance in a motor task and/or receives self-reported performance data. For example, a performance indicator may be processed for input to the apparatus by a performance reporting device. A performance reporting device may be, for example, a console configured to receive performance indicator data from the subject. The console is configured to measure a performance metric based on the finger individuation or to rate a performance in a game-based test.

In general performance data may be a measure or estimate of patient performance in a gross or fine motor task. For example, the performance data may include a measure or estimate of patient performance operating a tool (e.g., keyboard, joystick, toggle, buttons, etc.) that is connected to a performance reporting device. The performance reporting device may include one or more processors configured to test and/or score or monitor a patient in performing a task, including cognitive and/or motor tasks. The performance reporting device may be coupled to the performance indicator input or may be part of any of the apparatuses describe herein. A performance reporting device may include a display (video) an input (joystick, keyboard, etc.), and may include an output, which may connect to the performance indicator input. For example, the performance indicator input is configured to receive input from a game console.

In general, a performance indicator may include both objective and subjective indicators. For example, a performance indicator may include patient self-reported performance indicators and may be qualitative (good/bad, better/worse) or quantitative (e.g., scaled, 0-10, 1-100, etc.).

Examples of stimulator are provided herein. The stimulator may comprise one or more of: a haptic feedback a motion sensor, a position sensor configured to determine the position of a portion of the subject's body, etc. A stimulator may be configured as a wearable stimulator that is configured to be worn on a subject's arm and/or wrist, (e.g., and configured to apply stimulation to one or more of the subject's radial, ulnar and median nerves). A stimulator may include a housing enclosing the controller and wireless communication circuit and a shell configured to secure the housing against the subject's body. A stimulator may comprise one or more of: an optical output, a vibrotactile output or an audible output.

As will be described in more detail below, any of these apparatuses may include a training system in communication with the stimulator configured to provide training to the user before or during the application of electrical stimulation.

Any appropriate electrodes (surface, implanted, etc.) may be used. For example the electrodes may be configured to apply the electrical stimulation transdermally. The electrodes may comprise implantable electrodes.

The stimulator may include one or more controllers. For example, a controller may be configured to adjust the electrical stimulation by adjusting one or more of: intensity, current amplitude, frequency, duration, duty cycle, times/day, pulse duration, burst frequency, burst duration, or total treatment period.

In general, described herein are methods of treating a subject by closed-loop control of applied stimulation. These methods may be therapeutic treatments (e.g., treatment of stroke, gait dysfunction, brain injury, urologic disorders, etc.) or for non-therapeutic uses. For example, a method of treating a subject may include: applying a transdermal electrical stimulation to a muscle tissue; measuring a biomarker and/or a performance indicator from the subject; adjusting the transdermal electrical stimulation based on the biomarker or the performance indicator; and repeating the steps of applying, measuring and adjusting.

For example, the methods and apparatuses described herein may be configured to stimulate the radial, ulnar and median nerves (and/or other peripheral nerves) and to modify cortical control in the brain, which may enhance physical performance of athletes, professionals, and gamers or improve motor function (hand, finger and limb movement) in patients rehabilitating from neurological deficits and impairments caused by stroke, traumatic brain injury and other neurologic or non-neurologic conditions. One or more performance metrics may be taken from the training task (or game) and/or from a separate assessment task (or game) or period. A performance metric may include a measure of overall movement (e.g., tremor) and/or coordinated movement (e.g., rate of movement, accuracy of movement, independent control of finger moments, etc.).

Devices and algorithms for physical training and mental training (to improve memory and functional performance including motor coordination, limb-eye coordination, occupational and recreational skills) through periodic or sustained sensory electrical stimulation are also described. Devices and methods enable physicians and users to control their stimulation parameters and individualize their treatment plans based on one or more biomarkers. Methods and devices may be used alone or in combination with other devices and systems that enable patient-specific or personalized training. Learning and feedback techniques individualize treatment parameters depending on the subject's neurologic and motor function in diseased patients and healthy users.

Any of the embodiments of apparatuses described herein may include or incorporate (or may exclude) one or more features of any of the other apparatuses described herein, and/or may be configured to perform any of the methods described herein.

For example, described herein are methods of improving a subject's peripheral nerve function by closed-loop control of applied stimulation, the method comprising: applying an electrical stimulation to to a peripheral nerve; measuring at least one of: a biomarker or a functional performance indicator from a task that activates the peripheral nerve to which the electrical stimulation was applied; adjusting the electrical stimulation based on one or more of: the measured biomarker and the performance indicator; and repeating the steps of applying, measuring and adjusting.

A method of improving a subject's peripheral nerve function by closed-loop control of applied stimulation may include: applying an electrical stimulation to a peripheral nerve for longer than 10 minutes, wherein the electrical stimulation is sub-sensory or nearly sub-sensory performing a training task involving activation of the peripheral nerve; measuring at least one of: a biomarker from the subject and a performance indicator from the training task; adjusting the electrical stimulation based on at least one of the measured biomarker and performance indicator; and repeating the steps of applying, preforming, measuring and adjusting at least once per day for a plurality of days.

The electrical stimulation may be applied transdermally (e.g., through the skin) or via one or more implanted electrodes or adhesive patch electrodes (on the skin surface). Applying may comprise applying to at least one of: the radial nerve, the ulnar nerve and the median nerve. For example, applying electrical stimulation may comprise applying to the median and ulnar nerves (or just the median nerve, or just the ulnar nerve).

Any of these methods may include placing a wearable transdermal stimulator onto one or more of the subject's arm and hand. For example, applying may comprise applying electrical stimulation from a wearable wrist band, a patch, or a smart glove.

Measuring at least one of: a biomarker from the subject and a performance indicator may include measuring both the biomarker and the performance indicator. For example, measuring a biomarker may include measuring an electroencephalogram (EEG) from the subject, including measuring the change in EEG/power spectral density or spike-field coherence in the motor cortex of the brain, and/or measuring the change in delta or theta wave portion of the EEG.

In any of these methods and apparatuses, measuring the performance indicator may include determining a performance metric based on the finger individuation. For example, measuring a performance indicator may include rating performance in a game-based test, such as button press speed, individual button press speed, press accuracy, etc.

In general, any of the methods described herein may include performing a training task involving the normal biological "activation" (e.g., use) of the peripheral nerve being stimulated. For example, when stimulating the nerves innervating the fingers, the training and/or assessing period and/or task may include the use of the fingers. The training task may be performed during or immediately after applying the electrical stimulation.

In general, the applied electrical stimulation may be adjusted to increase or optimize the efficacy of the treatment. This adjustment is typically closed-loop, based on feedback from the subject's peripheral nerve(s) and/or from the body portion controlled or innervated by the peripheral nerve being stimulated. The adjustment may be continuous (e.g., based on feedback during or immediately after each stimulation) or periodic (based on feedback following 1, 2, 3, 4, 5, 6, 7, 9, 10, 11, 12, 15, 20, etc. or more stimulation sessions). Adjustment may be based on one or more indicators, as mentioned, including a biomarker (e.g., EEG signal) or performance metric. Any appropriate portion of the electrical stimulation parameters may be adjusted, including one or more of: intensity, current amplitude, frequency, duration, duty cycle, times/day, pulse duration, burst frequency, burst duration, or total treatment period. For example, adjusting the electrical stimulation may comprise increasing the intensity of stimulation.

In general, the stimulation may be limited to that which is sub-sensory or nearly sub-sensory, so that it is not felt (or barely felt, including detectable less than 70% of the time, 60% of the time, 50% of the time, 40% of the time, etc.) by the subject. Thus, any of these methods and apparatuses may be configured to maintaining the stimulation intensity as sub-sensory or nearly sub-sensory based on subject feedback. For example, the method or apparatus may include a user input or receiving a user input to decrease the intensity (e.g., amplitude, frequency, etc.) of the stimulation when applying the peripheral simulation if it is irritating or objectionable to the subject.

Any of these methods may be directed to methods of improving a subject's hand motor nerve function by closed-loop control of applied stimulation. For example, a method may include applying a transdermal electrical stimulation to one or more of the subject's radial, ulnar and median nerves; measuring an electroencephalogram (EEG) from the subject; adjusting the transdermal electrical stimulation based on the measured EEG; and repeating the steps of applying, measuring and adjusting.

In particular, any of these methods may be adapted for therapeutic use in patients recovering from stroke or other ailment. For example a method of improving hand motor nerve function of a subject recovering from a stroke by closed-loop control of applied stimulation may include: applying a transdermal electrical stimulation to one or more of the subject's radial, ulnar and median nerves; measuring an electroencephalogram (EEG) from the subject; adjusting the transdermal electrical stimulation based on a delta wave or theta wave component of the measured EEG; and repeating the steps of applying, measuring and adjusting.

In general, in any of these methods, repeating the steps (e.g., of applying, measuring and adjusting the electrical stimulation) may be repeated two or more times, e.g., 3, 4, 5, 6, 7, 8, 9, 10, 15, 20, 25, 30, 35, 40, 45, 50, etc. or more times, or on an ongoing basis.

In particular, also described herein are methods of improving a subject's performance on manual tasks involving finger individuation. For example, any of these methods may include: applying a transdermal electrical stimulation to one or more of the subject's radial, ulnar and median nerves; performing a manual training task involving finger individuation and estimating a performance metric based on the finger individuation; and adjusting the transdermal electrical stimulation based on the performance metric; and repeating the steps of applying performing and adjusting over a plurality of days. Such methods may be particularly (but not exclusively) helpful for training or improving performance in games involving hand coordination, such as video games.

Also described herein are apparatuses, which may include systems, devices, software, hardware, firmware, etc., for performing any of the methods described herein. For example, described herein are closed-loop apparatuses for improving a subject's peripheral nerve function, including: a stimulator having one or more electrodes, a power source, a controller configured to deliver an electrical stimulation from the electrodes and a wireless communication circuit, wherein the electrical stimulation has a set of stimulation parameters; a biomarker monitor; and a non-transitory computer-readable storage medium storing a program thereon, wherein the program causes a processor to: measure a biomarker from the biomarker monitor, and adjust the stimulation parameters based on the measured biomarker, and transmit the adjusted stimulation parameters to the stimulator.

The stimulator may be worn anywhere on the upper or lower extremity or inguinal area, and may be a wearable wrist band, patch, smart glove, smart sole, or leg anklet.

Any of these apparatuses, including the stimulator apparatus, may include one or more haptic feedbacks, such as vibrotactic feedbacks, pressure/compression feedbacks, temperature (cool/heat) feedbacks, or the like. Any of these apparatuses, including the stimulator apparatus, may include one or more sensors, including but not limited to one or more motion sensors, position sensors (e.g., configured to determine the position of a portion of the subject's body), or the like.

The stimulator may be a wearable stimulator that is configured to be worn on a subject's arm and/or wrist, and to apply stimulation to one or more of the subject's radial, ulnar and median nerves. The stimulator may be a smart sole that can be placed inside the subject's shoe and apply stimulation to one or more of the subject's leg or foot nerves. The stimulator may also be an anklet that can be placed around the subject's leg and apply stimulation to one or more of the subject's leg nerves. Lower extremity nerves that may be stimulated include the femoral nerve, sciatic nerve, inferior gluteal nerve, superior gluteal nerve, pudendal nerve. saphenous nerve, deep fibular nerve, superficial peroneal nerve, peroneal nerve, tibial nerve, lateral plantar nerve, medical plantar nerve, proper plantar digital nerves and the dorsal digital nerves of the foot.

In any of these apparatuses, the stimulator may include a housing enclosing the controller and wireless communication circuit and a shell configured to secure the housing (e.g., the one or more electrodes, which may be arranged on an outer surface of the housing) against the subject's body.

In any of the apparatuses described herein, although the electrical stimulation may be intentionally sub-sensory, the apparatus may include an output that provides a direct (including tactile or sensory) indicator that it is on and working. For example, the electrical stimulator may comprise one or more of: an optical output, a vibrotactile output or an audible output. The apparatus may be configured (e.g., the controller may be programmed) to provide such output, which may be variable, during the application of the electrical stimulation period (a period of time during which the electrical stimulation occurs).

Any of these apparatuses may include a biomarker monitor, as mentioned above. A biomarker monitor may include one or more electrodes for detecting biopotentials, e.g., electromyogram (EMG), electroocculogram (EOG), electroencephalogram (EEG), etc. For example, any of these apparatuses may include one or more electrical sensors (e.g., EMG sensors, etc.) as part of a biomarker monitor. The biomarker monitor may be separate from the stimulator, or it may be coupled or combined with the stimulator. For example, the same electrodes applying electrical stimulation may be used to detect/sense electrical activity in the subject, including in the subject's peripheral nerve(s).

Any of the apparatuses described herein may also include a training system. The training system may provide a training regimen (including one or more training games) to the subject before, during or after electrical stimulation. For example, any of these apparatuses may include a training system in communication with the stimulator configured to provide training to the user before or during or after the application of electrical stimulation.

In general, the apparatuses described herein may include control logic, such as software or firmware (including an application software or "app"), that controls all or a part of the apparatus, and may coordinate activity of the stimulator, including setting and/or modifying the applied electrical stimulation parameters, and/or training, and/or detecting a biomarker and/or detecting a performance metric. This software or firmware may be referred to herein as a non-transitory computer-readable storage medium storing the program, and may be configured to operate on a processor of a computer, including a wearable computer (e.g., a processor of a smartphone, smartwatch, etc.) or a hand-held device such as a tablet.

This control logic (e.g., software) may cause the processor to iteratively measure the biomarker, adjust the stimulation parameters and transmit the adjusted stimulation parameters.

For example, a closed-loop apparatus for improving a subject's peripheral nerve function may include: a stimulator having one or more electrodes, a power source, a controller configured to deliver an electrical stimulation from the electrodes and a wireless communication circuit, wherein the electrical stimulation has a set of stimulation parameters; a training apparatus; a biomarker monitor comprising an electroencephalogram (EEG) monitor; and a non-transitory computer-readable storage medium storing a program thereon, wherein the program causes a processor to measure a delta wave or theta wave component of an EEG from the biomarker monitor; and adjust the stimulation parameters based on the measured biomarker; and transmit the adjusted stimulation parameters to the stimulator.

An apparatus for enhancing performance on manual tasks involving finger individuation by closed-loop electrical stimulation may include: a stimulator adapted to be worn on user's arm, hand or arm and hand, the stimulator having one or more electrodes, a power source, a controller, wherein the stimulator is configured to deliver an electrical stimulation from the electrodes to one or more of the user's radial, ulnar and median nerves when worn; a non-transitory computer-readable storage medium storing a program thereon, wherein the program causes a processor to: present a manual training task involving finger individuation, estimate a performance metric based on the finger individuation, adjust the electrical stimulation based on the performance metric, and transmit the adjusted stimulation parameters to the stimulator.

In general the methods described herein may be referred to herein somatosensory electrical stimulation (SES) methods and any of these apparatuses may include or be referred to as SES systems.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 2A, 2B, 2C, 2D, 2E, 2F, 2G and 2H show different embodiments to assess EEG activity in users before, during or after stimulation. An EEG monitor may be one form of feedback monitor that may be used herein.

FIGS. 6A, 6B and 6C show examples of wrist-band devices that may stimulate the radial, ulnar and median nerves in the wrist. In FIG. 6A a wrist-band device that stimulates the radial, ulnar and median nerves in the wrist includes nerve stimulating electrodes, sensors for hand/limb movement, battery and related electronic circuitry, and wireless sensor for connectivity to a display and/or EEG biomarker signal from the brain. FIGS. 6B and 6C illustrate other variations of such devices.

FIG. 6D is a schematic illustration of a circuit diagram for a device similar to those shown in FIGS. 6A-6C.

FIGS. 7A-7B show alternative embodiments of devices to be worn on the wrist containing electrodes for applying stimulation as described herein.

FIGS. 8A-8C shows other examples of devices for peripheral nerve stimulation in the form of an electronic patch that can be placed on the surface of the body.

FIG. 9 illustrates a touch screen may be used to train fine motor (pinching, tapping, individuation) skills through gamification.

FIGS. 10-13 list various conditions, target PNS sites and treatment plans including training and feedback that can be treated with the apparatuses described herein.

FIG. 14 lists potential groups of users that could benefit from PNS sites and training/feedback systems that may find use.

FIG. 15A lists examples of stimulation parameters that may find use in the apparatuses and methods described herein.

FIG. 15D illustrates an example of a burst mode of stimulation using any of the apparatuses and methods described herein, in which stimulation intensity is relatively high (e.g., 1000 Hz) but then interrupted periodically (e.g., 2-3 Hz). It is possible to titrate A-beta sensory fibers via this method. The methods and apparatuses described herein may further titrate parameters (e.g., pause frequency between 0.1-50 Hz, intensity of burst between 100-1000 Hz) based on cortical parameters. Other parameters may include pulse duration, which may differentially affect sensory fibers. For example, 60-150 microsecond pulses may be better for sensory, while 150-200 may be better for motor. The apparatuses and methods described herein may modulate pulses between 25-500 microseconds to optimally titrate motor parameters.

FIG. 16 lists several outcome measures that may be assessed and used to adjust stimulation parameters.

FIG. 17 shows a representative change in EEG in a subject treated with the devices described herein (top is before, bottom is after).

FIG. 18 shows improvements in finger coupling index (FCI) in treated patients with stroke.

FIG. 19 illustrates the results of kinematic and clinical outcome measurements in patients with stroke treated with the devices described herein.

FIGS. 25A-25B and 26A-26B illustrate devices and systems to measure response to PNS.

DETAILED DESCRIPTION

Disclosed herein are various embodiments of a closed-loop feedback system wherein SES parameters can be titrated to tailor parameters to individual subjects. Certain embodiments of the system aim to use both physical performance metrics as well as neurophysiological biomarkers such as EEG to optimize SES.

How existing neural dynamics interact with peripheral stimulation and how this interaction correlates with EEG information and motor recovery is of great interest. The data suggest notable differences between responders and non-responders before and after SES. Of interest is the development of a novel device and algorithm that delivers SES using EEG to dynamically vary treatment parameters and to automatically terminate stimulation when maximal gains in functional performance (e.g., limb movement in stroke patients and response or reaction time in healthy subjects) and/or changes in the motor cortex are achieved in a single treatment session or a series of treatments. The present invention describes methods, devices, systems, therapies and algorithms that overcome such limitations. The ability to modulate or modify cortical signals offers a robust path for individualization of parameters for patient treatment.

As described in further detail below, 8 patients were tested using a TENS unit for SES and external computers for real-time data processing. It was discovered that low-frequency oscillations (LFO, e.g., 0.4-4; 4-8; 8-12 Hz) in the contralateral hemisphere of the brain are modulated by SES. Importantly, the extent of the motor response after SES could also be predicted after treatment. Therefore, LFOs can be used to titrate SES stimulation timing and dose, using for example a closed-loop device that uses EEG signals to control the extent and timing of SES.

Various aspects of the apparatuses and methods, including target nerves and locations, systems, devices and embodiments are described below.

Figure 1:
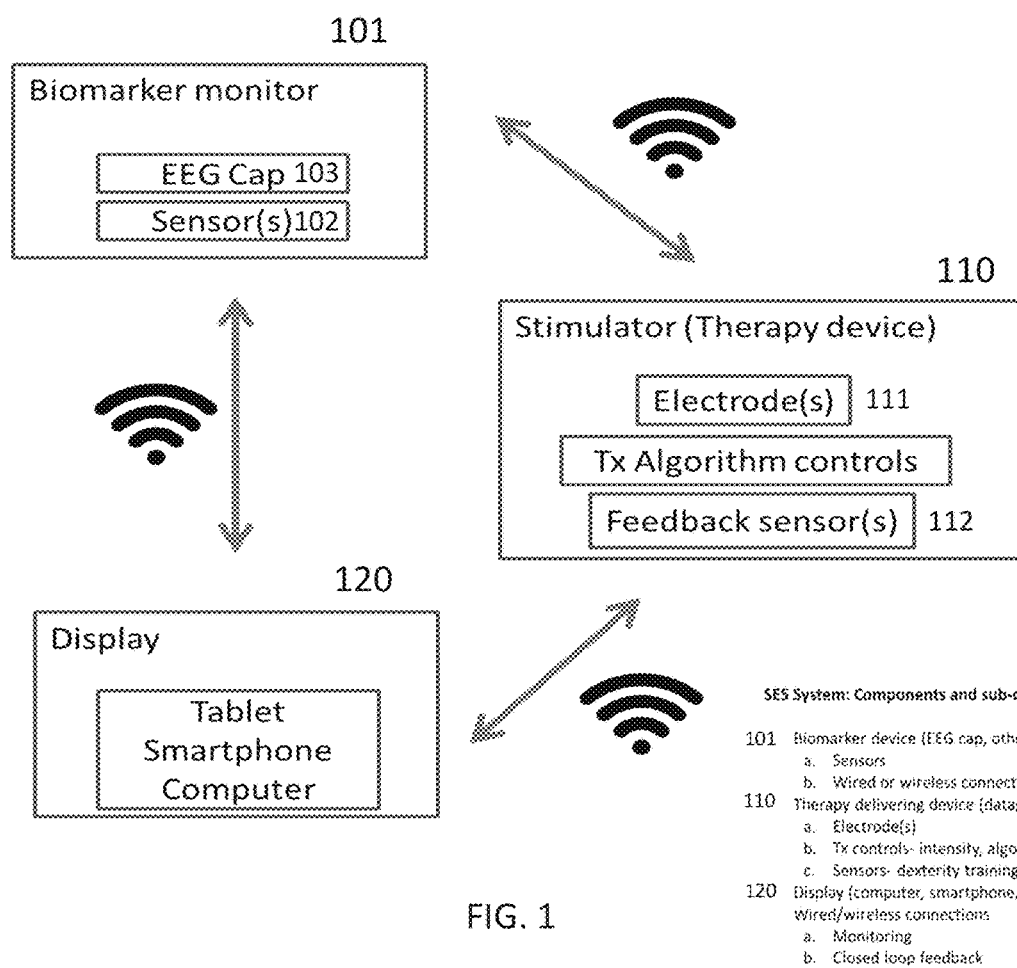
FIG. 1 shows a generic somatosensory electrical stimulation (SES) system with three components (feedback monitor or "biomarker" monitor, stimulator apparatus, and display, each of which may be wirelessly connected to the others) that can be used to treat medical or non-medical conditions.

The first embodiment comprises an SES device and/or system with at least three components as shown in the FIG. 1. The first component consists of a biomarker monitor 101 to monitor the biomarker levels at baseline (pre), during (peri) and after (post) stimulation. The sensor(s) 102 may be one or more electrodes attached to the head (outer skin surface of the skull, or other biomarker feedback sensing locations inside the body) or incorporated into a smart cap 103 that may be worn by healthy and diseased subjects. The sensor signal may be the amplitude of EEG current and frequency.

Other embodiments and forms for devices may be conceived. The biomarker monitor 101 could be a removable adhesive patch with a sensor that can be placed on various locations on the body depending on the biomarker activity being measured. FIGS. 2A-2H show alternative embodiments of the biomarker monitor 101. The biomarker monitors 101 may be incorporated into eyeglass frames, specifically along the inner contact surfaces of the arms that touch skin behind the ear, into an earplug/earphone with a hook that can be placed around the ear lobe, similar to a Bluetooth wireless communication device. In some cases, the eyeglass frames may be supplied with disposable conducting films. The biomarker monitors 101 may also be incorporated into audio headsets that are in skin contact covering the ears. The films may be wrapped around frame surfaces (to improve electrical contact) and may be disposed after use. Similarly, other measures of brain activity, nerve activity and muscle activity may also be monitored for biomarker feedback.

A second component may include the stimulator (therapy device) 110 that comprises one or more electrodes 111 that deliver electrical pulses locally near peripheral nerves of interest. One or more electrodes 111 may be activated for SES nerve stimulation and electrical pulses may be delivered using a hand-activated push-button mechanism or a remote device (smart phone or tablet computer) using an application or software program. The stimulator 110 may be integrated into various functional forms, devices or products such as a hand glove, wrist band, arm band, an anklet, leg band, a disposable patch with an inset to insert a rechargeable and reusable (or alternatively a disposable or one-time use) electrical stimulator, etc. The proposed device (hand glove, wrist band or patch) must be comfortable during wearing and maintain good electrical contact with skin to deliver the appropriate stimulus, without injury or damage to the skin. The device may incorporate additional feedback sensor(s) 112 to stimulate and/or detect hand motion, finger movement, and measure motor/limb function to provide dexterity training and haptic feedback during SES treatment.

The stimulator component may also be incorporated into existing devices that monitor vital signs like temperature, heart rate and blood pressure (such an iWatch or similar devices) or walking motion (pedometers, like FitBit etc.). The stimulator may be attached to or otherwise be connected to any or all parts of a watch or fitness band, including the display portion, one or more straps and/or latches, so long as the stimulator is placed near or on the skin or nerve. It may be integrated and programmed to apply various therapeutic algorithms to achieve desired functional performance using existing display, communication and user interfaces.

Figure 3:
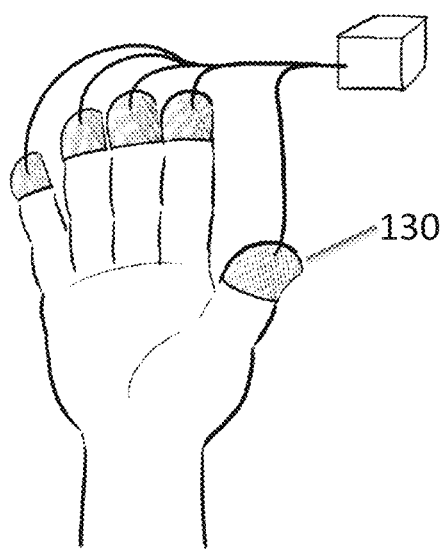
FIG. 3 shows an example of one variation of an apparatus worn on the fingers of a user to assess finger motion.

A feedback sensor 112 may take different shapes and forms. They may be incorporated into the smart glove. However, wearing and removing a glove may be difficult for stroke patients that have limited hand movement. To overcome this limitation, the feedback sensors 112 may be incorporated into stretchable/elastic rings (made from polymers) that incorporate the sensors and detect hand and digit motion. The feedback sensors could also be in the form of elastic/stretchable finger caps 130 (made from polymers), as shown in FIG. 3, that incorporate sensors to detect motion, response time and reaction time, velocity, etc. Multiple rings and caps may be worn to measure the individual movements of each finger and/or limbs. These feedback sensors that detect the feedback response to SES stimulation may be wirelessly integrated to communicate and/or interact with the SES stimulator or the electronic display systems A third component may include a display system 120 (in some variations a training system or training and/or assessment system) to visualize all signals that are being monitored, delivered or captured as feedback. Biomarker EEG signals from the brain may be displayed along with the SES stimulation parameters during stimulation. Feedback from nerves, limbs and brain function during or after stimulation may be displayed. The display could be a computer screen, tablet screen or a smart phone with touch screen controls. In addition, the touch screens on the display may also be used to provide dexterity training to healthy and diseased subjects to enhance their performance, which may include motor function, motor coordination, limb movement, memorization, etc. Display system 120 may also comprise an interface to control stimulation parameters (like intensity, frequency, time, etc.) or select pre-specified algorithms for treatment. The treatment algorithm may also be adaptively developed based on patient disease condition, biomarker response to treatment and functional response to treatment. SES stimulation may be done with or with training/learning feedback.

In some embodiments, display system 120 may also comprise video gaming software to train patients and healthy subjects to enhance their motor function or skill levels. Different games may be envisioned to treat different disabilities of the leg or hand in patients that have limited limb movement and suffer from neurological deficits. Games may be adapted to individual patients depending on their degree of limb movement. Similarly, different games of different intensity levels may be prescribed to improve the performance and/or reaction and/or response time of gamers, athletes and other professionals.

Another component, which may be integrated into all or some of the other components, may be connectivity software and feedback circuits to form a closed-loop system to monitor and titrate dosing and optimize training. The biomarker device, stimulator and display may be connected by wires or communicate using wireless protocols. In addition, software enables real-time feedback on motion during dexterity training. The feedback may be used for adaptive learning and selection of individualized SES parameters and to titrate dosing (intensity, timing, duration and duty cycle) for SES stimulation. Data and signals may also be collected and transmitted to electronic health records (EHR) or electronic medical records (EMR).

Figure 4:
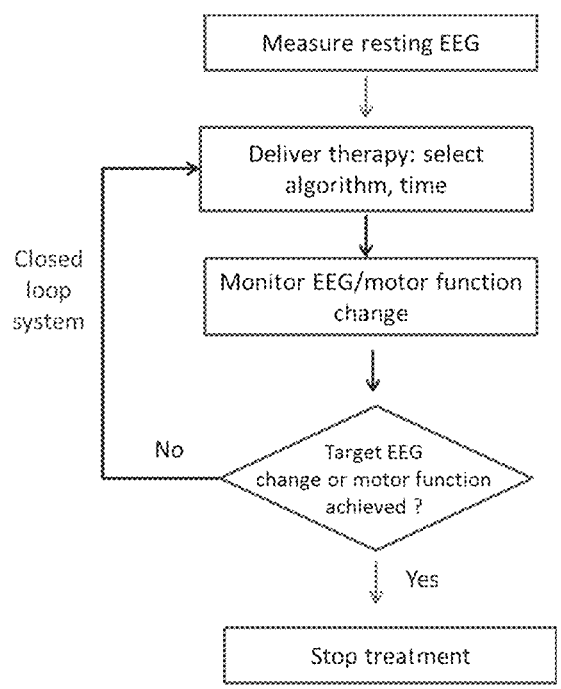
FIG. 4 shows a schematic of one variation of a closed-loop SES system that also includes feedback (e.g. via one or more biomarker).

Another embodiment of a closed loop system with a biomarker (EEG) device and stimulator to treat pain or other conditions, is shown in FIG. 4. The resting EEG in a subject may be measured and SES may be delivered and feedback signals monitored for change in EEG activity or motor function, or motor response etc. If the targeted range of levels are not reached or the desired SES biomarker signal is not activated, a different set of stimulation parameters (intensity, pulse width, frequency, time, etc.) may be selected until the desired therapy is delivered. Alternatively, the device may be repositioned to a different nerve location and the procedure repeated until desired effects are achieved.

Smart Glove Embodiment

Figure 5:
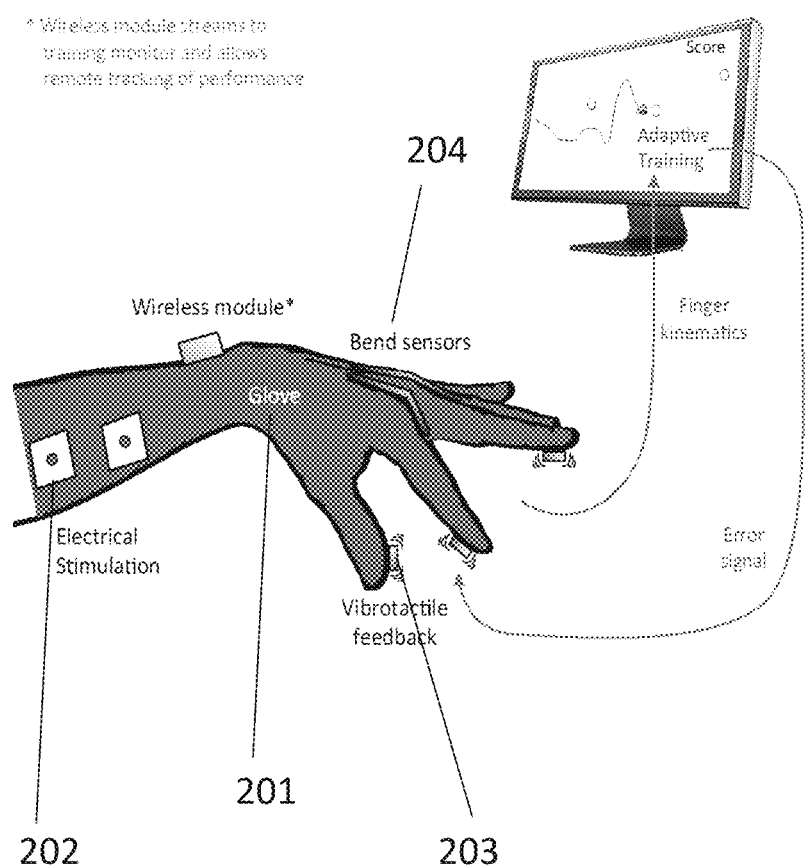
FIG. 5 shows one embodiment of a glove that can be used during task training.

FIG. 5 shows another exemplary embodiment of the system. In this case, a wearable dataglove 201 incorporates electrical stimulation of the three peripheral nerves of the arm, namely the radial, median and ulnar nerves. The device comprises bipolar electrodes 202 as well as vibrotactile feedback sensors 203 to provide real-time feedback regarding (EEG or motor or movement) response to SES stimulation and task-errors during dexterity training. This modular unit also has the capacity to monitor finger movements (using bend sensors 204), ability to electrically stimulate all three nerves at a range of frequencies, and be able to provide vibratory cues based on real-time monitoring of performance. This system combines an adaptive gaming environment that can be customized for each patient. Importantly, this system also has the capability to allow physicians, physical therapists and other professionals to remotely monitor each patient's rehabilitation trajectory.

Smart Sole or Sock Embodiment

The smart glove embodiment may be adapted into a smart sole, that can be inserted into the shoe of a subject, or a smart sock, that can be worn by the subject, to stimulate the peripheral nerves of the leg. The sleeve or sock comprises bipolar electrodes, vibrotactile feedback sensors, bend sensors etc. similar to the smart glove. Both embodiments may be combined with an adaptive gaming environment and customized for each subject to enhance their limb performance. In healthy subjects or athletes, this may improve their reaction time and running speed. In stroke patients that have compromised limb function, the stimulation may help recovery of limb movement and function. Other embodiments, such as a smart shoe, may also incorporate the sensors, stimulators and electronics to achieve the desired SES and improve functional performance.

Wrist Band Embodiment

FIGS. 6A-6D and 7A-7B show other potential components of exemplary apparatuses configured as wrist bands that incorporate the various elements described above. In FIG. 6A-6D the wrist band 250 incorporates one or more electrodes 255 to individually or collectively stimulate the three peripheral nerves of the arm, namely the radial, median and ulnar nerves. The device may also comprise bipolar electrodes as well as vibrotactile feedback sensors to provide real-time feedback regarding hand or motor or movement response to SES stimulation and task-errors during dexterity training. It has the capability to electrically stimulate all three nerves, separately or collectively, using different algorithms at a range of frequencies, intensities and pulse widths to achieve desired performance. Similar embodiments may be made to stimulate the nerves in the lower extremities and other parts of the body.

The wrist band 250 is made from a stretchable elastic polymer that enables the electrodes to have good skin surface contact at all times during stimulation. The polymer may be impregnated with conductive gels and/or biocompatible materials to maintain good electrical contact and minimize skin sensitivity. The polymer incorporates all electronic circuitry including the electrodes, wireless sensors, stimulator and a battery. It may also have a miniature console or electronic display to indicate stimulation on/off, battery level, and stimulation parameters. It may also incorporate a miniature touch pads/buttons to turn the system on/off, select the intensity of stimulation and select the algorithm for SES stimulation. Alternative embodiments of a wrist band device can be seen in FIGS. 7A-7B.

The device and system may be combined with an adaptive gaming environment that can be customized for each patient or subject. The system may have the capability that will allow subjects to individually select their stimulation algorithm, adjust the time of treatment, collect and store data on stimulation parameters and duration of stimulation every day, for days and months. The data may be downloaded onto a computer, tablet or smartphone using standard wireless communication protocols and standards. In addition, the device has the capability to connect with EMR/EHR so that physicians, physical therapists and other professionals to remotely monitor each patient's rehabilitation trajectory or subject's functional performance.

The wrist band embodiment may also be adapted into a leg band or an anklet that may be placed at various locations on the leg surface to stimulate different peripheral nerves of the leg, such as the sciatic, femoral, saphenous, tibial, obturator or peroneal nerves. It may be integrated with an adaptive gaming application, with a smart mat to sense subject motion, to monitor feedback to stimulation and titrate treatment parameters.

Electronic Patch Embodiment

FIGS. 8A-8C shows other embodiments of an exemplary device and system in the form of an electronic patch that can be placed on the surface of the body, adjacent to any peripheral nerve or nerves, and stimulate them using SES. The patch is adhesively attached to the body using biocompatible and/or bioconductive gels and other materials to send electrical signals, monitor nerve activity, assess motor function, and other human functional parameters of interest. The electronic patch comprises one or more electrodes to individually or collectively stimulate the different peripheral nerves. The patch is in wireless communication with a computer, tablet or smart phone device to control SES, obtain feedback, collect data, store and develop adaptive feedback to titrate the dose for treatment effect.

As shown in FIG. 8A, the SES device may be fabricated as reusable integrated system comprising the patch electrodes for stimulation, electronics to generate electrical pulses, feedback sensors to measure biomarker response, and other feedback sensors to monitor movement and functional performance, a battery and a wireless communication module. Here the electrodes and stimulation electronics are integrated as system and the patch can be adhesively attached to the skin at different parts of the body to stimulate nerves and muscles. For example, the device may be placed near the trigeminal nerve on the face. Stimulation may be initiated to monitor the EEG biomarker response using feedback sensors in the device or an external electronic-cap, titrated to achieve the desired motor or functional response. Sub-sensory electrical stimulation is delivered for a given duration, data collected, SES device turned off, removed and potentially reused again. The system also incorporates the power supply, wireless interface and other general features as described above.

A second configuration is shown in FIG. 8B, where the patch comprising the electrode for SES is separate from the electronic stimulator and console. An advantage of this system is its disposable nature of the patch electrode used for contact and stimulation purposes only. The disposable patch contains the electrodes or conducting materials/surfaces that enable/improve the conduction by maintaining contact, provide stimulation and measure feedback. As with other embodiments, it comprises a slot to insert the stimulator and related electronics (battery, sensors and wireless communication console) for SES. The stimulator may also be recharged periodically and is not a disposable. The reusable stimulator contains electronics components and circuitry for stimulation, sensing, communication and control using a wired or wireless connections. This offers the advantage of designing a small and simple patch device that is concealed and low profile.

Patches of different form and function may be used to stimulate nerves in different parts of the body using the same stimulator. The disposable patches may be made from a combination of a stiff plastic material that take the shape of the contours in the body combined with soft, elastic and conductive coatings that maintain electrical contact with the body. The hard polymer preform of the patch with the slot may be injection molded or formed (using web converting) and a thin adhesive conducting film may be attached to the hard polymer preform to enable electrical contact between the skin, electrodes and the stimulator. Alternatively, the user may apply conductive gel under the stimulator or electrode. A patch may have multiple polymer preforms or slots, allowing for more than one stimulator or electrode to be supported by a single patch. For example, a single electronic patch system may have two or more slots that hold in place multiple electrodes placed near the ulnar and median nerves for the management of stroke.

Specifically, such a device may be placed on the trigeminal nerve on the facial surface to treat migraines, on the back to relieve pain or on the perineum to treat erectile dysfunction or incontinence. The electronic patch system may also comprise of one or more patch electrodes to stimulate nerves at one location in the body and vibrotactile feedback sensors to provide real-time feedback regarding limb movement (motor function or functional performance parameter) to SES stimulation in a different part of the body. The disposable patches may also be placed on the wrist to treat stroke patients and on the back to treat pain or other diseases and conditions.

Training/Haptic Embodiments

Other form factors of devices with sensors to detect movement in limbs and fingers include rings that can be placed on different fingers. The rings contain sensors that work in conjunction with (or may be connected to physically or wirelessly) a wrist-band PNS stimulator and a smart phone or tablet. SES or PNS is stimulated through the wrist band electrodes while the patient moves the fingers based on a game on the smart phone or tablet. The finger ring sensors detect motion and measure stimuli and record data for each session. Based on the stimulation parameters and feedback on achieved movement, the stimulation can be titrated to achieve the desired outcome or limb movement in a single session or multiple sessions during physical treatment and rehabilitation lasting a few weeks to months. A similar system may be used to enhance the response time of video gamers by SES with or without training them using different video games. Various tests, like the 9-hole peg test, may be used to measure the response time.

As mentioned previously, FIG. 3 shows an embodiment or form factor to monitor finger and/or limb motion that involves the use of small finger caps that detect motion before and after SES or during training with video games. These finger caps can be easily worn and removed by patients that suffer from stroke and other neurological deficits. SES or PNS is stimulated through the wrist-band electrodes while the patient moves the fingers based on a game on the smart phone or tablet. The finger caps containing sensors detect finger motion, measure stimuli and record data for each session. In another embodiment, the finger caps may also be adapted to fingers in the leg and work in concert with an ankle bracelet stimulator. Rings, anklets and caps may also contain electronics components and circuitry for stimulation or sensing, may communicate with and be controlled by the smart-phone or tablet using wired or wireless connections.

EEG Feedback Embodiments

The EEG device and electrode for the system are designed to be user friendly and are available in a variety of embodiments as previously shown in FIG. 2. These EEG feedback and/or stimulation systems may be integrated with Bluetooth Low Energy (BLE) or similar wireless communication technology with phone to minimize bulk by transferring as much processing to software/phone as possible, which may also improve interpretation. Electrode systems for stimulation use conduction gels (standard EEG paste) that have the potential to cause injury or damage to the skin. To minimize such damage, the systems may comprise a high-cohesion adhesive gel with minimal residue (e.g., maybe similar to material used in reusable lint rollers or the material used on dashboard suction mounts for cell phones, made by 3M or 'sticky hand' toys where the dust can be washed off).

Training/Feedback Game Hardware Embodiments

Although a major component of training is related to motor tasks, additional components (lights, sounds, images, on screen indicators, vibration) may provide additional cues to reduce cognitive burden, similar to the haptic feedback in the glove as previously described. Biofeedback systems are also used for monitoring and controlling chronic pain. Feedback systems to enhance performance during training/game playing include visual, vibration and sound on a mobile phone/tablet. The touch screen may be used to train fine motor (pinching, tapping, individuation) skills as shown in FIG. 9. In FIG. 9, the user taps her fingers as directed by the game, with each finger tapping the screen of the tablet or phone individually. In addition, existing motion sensors with tablets and phones may be used, when possible to obviate the need for additional sensors, particularly for gross motion/large muscle. For example, in essential tremor, holding the phone while reaching may be used to measure tremor using the gyroscope in the smart phone. Similarly, existing vibration/sound sensors and images/lights may be used to provide additional feedback during training sessions, analogous to haptic feedback from glove. Hardware may be used to coordinate input and output from other devices/sensors/electrodes. Software and internet connections may be used for algorithm implementation, cloud relay, etc.

In some embodiments, training and feedback hardware may be integrated into the electrode device. Position/motion sensors may be built into a wrist band for example. Vibration/sound/light feedback may be built into the device and/or system. For large muscle training, a leg sleeve can measure biking/running speed and give vibration feedback when rate falls below a target level. In essential tremor patients, the wrist device can measure tremor and vibrate or beep to give feedback. In some embodiments, there may be a VR headset which uses visual and/or sound and/or haptics. Google Glass or haptic gloves that monitor vibration, movement and temperature may fine use. Feedback stimulation though the electrodes themselves or supra-sensory feedback may be used as well as headphones/sound. Alternatively, motion capture using Microsoft Kinect (nuanced motion or gait analysis) or Nintendo Wi may also find use.

Feedback sensors can be integrated into the hardware, using bluetooth low energy or similar wireless technologies for communication with phone or electronic medical records or cloud-based data collection, storage and management systems.

Training games may also be used to treat pain/perception syndromes (RSD, trigeminal neuralgia, nausea, vertigo etc.). A phone or tablet may provide a biofeedback training system. If the software progressively distracts the subject and then refocuses them on the symptom while they dynamically rate their pain, one could "gamify" the ability to supratentorially control their pain. This might actually be a useful technique for chronic pain in and of itself. The app can provide instructions (visual and auditory) for measuring response to therapy. "Look at a spot on the wall approximately 20 feet away for 60 seconds, now . . . , how do you rate your . . . " essentially replicating an interview or assessment.

Treating Various Conditions/Performance Enhancement

Various diseases and conditions may be treated by PNS combined with training and feedback using the devices, systems and algorithms described above. These include stroke, pain, neuralgia, migraines, gait disturbances, Parkinson's disease (PD), etc. Although PNS is not expected to change course of the disease, PD patients may find that physical therapy ameliorates symptoms (mobility, posture, gait, stiffness), but benefits are lost if physical therapy is discontinued. The current invention would allow long term treatment at home. PNS may benefit nerves in large and small muscles, particularly large. PNS may also treat impotence from non-vascular causes. Various conditions, target PNS sites and treatment plans including training and feedback are detailed in FIGS. 10-13. PNS may also be used to enhance performance in healthy subjects. Professional athletes, dancers, musicians, physicians, gamers, transcriptionists and stenographers can either enhance their professional or occupational skills or prevent the deterioration of motor function from repetitive motion through PNS and feedback algorithms. In addition, PNS may also be used to improve memory and sleep. Subjects that can benefit from treatment, target PNS sites and training/feedback systems are detailed in FIG. 14.

Various nerves may be targeted for treat disease conditions or to enhance performance. These include nerves of the upper limb such as radial nerve (all branches), median nerve, ulnar nerve, cutaneous nerve (single fingers, whole hand, forearm), lateral cutaneous nerve of forearm, supraclavicular nerve, axillary nerve, posterior branch cutaneous nerve, and the medial brachial cutaneous nerve. Nerves of the lower limb include common peroneal nerve and its branches, sciatic nerve, superficial branch, branches of the tibial nerve, saphenous nerve, sural nerve, lateral femoral cutaneous nerve, lateral calcaneal, medial calcaneal, superficial peroneal, lateral femoral cutaneous nerve, cutaneous branches of L1-L4, S1-3. Sacral nerves include those supplying the S1-S3 dermatomes and the pudendal nerve. Facial nerves include the trigeminal nerve and branches, occipital nerve, superficial cervical plexus, branches of the facial nerve, branches of the cervical nerve and cranial nerves I-XII. Any combination of nerves may also be used to treat any of the conditions listed herein. For example, one embodiment may simultaneously stimulate the median, ulnar and/or radial nerves. Other embodiments may stimulate the sural and the deep peroneal nerves. These examples are not meant to be limiting.

In the case of stroke, traumatic brain injury or other acquired brain injury with speech, language, dysphagia, upper-limb and lower-limb deficits, or cerebral palsy, the device may stimulate nerves of the upper limb (sensory and motor nerves C3-T2, including ulnar, median, radial, axillary, cutaneous nerves of the arm, lateral cutaneous nerve of forearm, or brachial cutaneous nerves, with efficacy assessed through finger kinematics, hand opening and closing, finger tapping, or interactions with a game or phone. The device may stimulate the lower limb (e.g. S1-S5; L1-5; branches of sciatic such as tibial and peroneal, femoral, obturator, saphenous, foot cutaneous nerves or plantar surface nerves with efficacy assessed using a bracelet at the ankle that can monitor step length, stride, gait speed or stance, motion capture of speed or use of camera to measure speed. The device may stimulate oromotor nerves (cranial nerves 3-12, pharyngeal nerves, cutaneous nerves in mouth with assessment of speech and dysphagia using subjective assessment, recording of speech or swallow tests.

For gait disturbances, including age related decline in gait parameters, sensory neuropathy, gait ataxia from cerebellar defects and neuropathy, Parkinsonism and small-vessel ischemic disease, stimulation of the girdle for gluteus minimus or use of leg/thigh sleeves for lower extremity may be used. Assessment of efficacy may involve placing a cell phone in a pocket on the girdle (likely horizontal in the midline) and using analysis of phones integrated with motion sensors to analyze gait and provide feedback, placing motion sensors in critical locations along the lower extremities using adhesives or integrated into girdle/sleeves or using motion capture (using e.g., Microsoft Kinect).

For Parkinson's disease, various small and large muscles may be stimulated. Assessment of efficacy may involve use of motion capture or motion sensors to look at gait, tracking of smoothness and responsiveness of finger motion as a patient traces his finger on a tablet or a game such as chasing a character running through a maze on the screen. The speed and complexity of the maze could be modulated and titrated to the patient's ability and response to PNS.

For essential tremor, nerves of the wrist may be stimulated, with assessment of efficacy via a haptic glove or a mobile phone using motion sensors within the phone to detect tremor and sound/vibration of the phone as sensory feedback to patient.

For senile loss of proprioception or decreased ability to respond to imbalance, nerves that innervate large and small muscles may be stimulated, provided with balance training and balance recovery to decrease likelihood of falls. A sensored mat or a cell phone in a pocket can be used to measure gait parameters (e.g., stumbles) during regular walking or standing or standing with eyes closed.

For upper motor neuron degenerative disease like primary lateral sclerosis, ALS, multiple sclerosis, spinal cord injury, stimulation of nerves as previously described for stroke can be delivered. Assessments could include measures of spasticity or speed of movements of the upper and lower extremity. Accelerometers may be used to detect changes in function.

For post-polio syndrome and other lower motor neuron diseases such as ALS, lower and upper extremity electrodes may be used to target specific affected limbs or other nerve targets as previously described for stroke, with assessments including self-report of fatigue or pain, or the use of a force transducer to measure force and muscle strength.

For neurological movement disorders such as tics, chorea, hemi-ballismus, ataxia, and rigidity, stimulation of fine motor and large muscle groups may be delivered or the device may stimulate nerves of the upper limb (sensory and motor nerves C3-T2 including ulnar, median, radial, axillary, cutaneous nerves of the arm, lateral cutaneous nerve of the forearm, or brachial cutaneous nerves or nerves of the lower limb (e.g., S1-S5; L1-5, branches of sciatic such as tibial and peroneal, femoral, obturator, saphenous, foot cutaneous nerves or plantar surface nerves). Assessment of efficacy may include subjective assessment or objective assessment using an accelerometer or other sensor.

For restless leg syndrome, periodic limb movements or periodic limb movements of sleep, stimulation may include the lower extremity muscles and sensory/motor nerves (e.g., S1-S5; L1-5, branches of sciatic, femoral, obturator, saphenous nerves). Assessment may involve subjective assessment or objective assessment with an accelerometer, gyroscope or EMG electrode.

For muscle cramps, the device may stimulate the lower extremity muscles and sensory/motor nerves (e.g., S1-S5; L1-5, branches of sciatic, femoral, obturator; saphenous) or nerves of the upper extremity. Assessment may be subjective.

For trigeminal neuralgia, an adhesive facial electrode may target cranial nerve 5 and/or 7 and associated sensory nerves with assessment primarily subjective based on patient report. An adhesive facial electrode that innervates one or more cranial nerves 1-12 may find use in the treatment of Bell's Palsy, facial spasm or blepharospasm.

For migraine or chronic vertigo, an adhesive facial electrode may target cranial nerves 5 and/or 7 and associated sensory nerves, occipital nerve, or auricular nerve with assessment based on self report (e.g., headache duration, frequency and severity for migraine).

For reflex sympathetic dystrophy, the device may comprise an electrode on a sleeve or band worn around the wrist. Feedback could involve use of an LED and sensor to measure blood flow (like pulse ox) or the use of a biofeedback app.

For the treatment of dysphagia, the device may stimulate the trigeminal, pharyngeal surface, upper esophageal, or vagus nerves with assessment of efficacy via self report or objective testing such as fluoroscopy or swallow tests.

For torticollis, the device may stimulate the sternocleidomastoid muscle, cranial nerves 5, 7 and associated sensory nerves, the occipital nerve and/or auricular nerve, with assessment via self report, accelerometer, or EMG recordings.

For impotence, the perineum (pudendal nerve) may be stimulated. Subsensory stimulation may be preferred. Assessment could involve sensors to measure blood flow or stretch sensors.

For premature ejaculation, stimulation may involve cutaneous nerves associated with S1-5 and perineal nerves, the pudendal nerve and its branches.

For urinary incontinence, spastic bladder or overactive bladder, stimulation may involve cutaneous nerves associated with S1-5 and perineal nerves, the pudendal nerve and its branches. Assessments could involve self-reported symptoms related to reduced spasticity, improved bladder tone, or frequency of voiding.

For pelvic floor dysfunction, a perineum adhesive electrode may be used to provide stimulation, including subsensory stimulation.

For insomnia and other sleep disorders, an adhesive facial electrode targeting cranial nerves 5 and/or 7 and associated sensory nerves, occipital nerve, auricular nerve may be used as well as stimulation of the upper and lower limb targets previously identified for stroke. The stimulation may be tailored to sleep cycles of the user. Assessment may involve self report or EMG, EOG or EEG.

For low back pain, including sciatica, lumbar radiculopathy and peripheral neuropathy, the device may stimulate nerves of the lower limb (e.g., S1-S5, L1-5, branches of sciatic such as tibial and peroneal, femoral, obturator, saphenous, foot cutaneous nerves or plantar surface nerves).

For obstructive sleep apnea, the device may stimulate the hypoglossal nerve with assessment of AHI, ODI and snoring to determine efficacy.

Athletes, dancers, musicians, physicians, surgeons, video game players and typists may all find benefit from the devices described herein. Electrodes may be placed in sleeves for the arm, leg, wrist, etc. to provide requisite stimulation in an easy to use, comfortable delivery system.

Methods and Algorithms

PNS electrode stimulation is modulated based on feedback from EEG as well as training/feedback "game". This may be further modulated and optimized based on how people with similar EEG profiles and responses performed in the past. For example, the treatment algorithms of later patients is adjusted or informed by feedback data from patients treated earlier. Alternatively, treatment algorithms for the same patient may be personalized based on their response to PNS, and/or adjusted or titrated in subsequent sessions to further enhance treatment or performance. For extended stimulation (e.g., sub-sensory or nearly sub-sensory that runs intermittently during the day or overnight) stimulation is algorithmically optimized while wearing EEG but can be continued without. For example, the patient may wear the EEG for an hour to update/optimize the stimulation paradigm, which then continues with EEG cap off. Intensive PNS treatment algorithms may be prescribed with EEG cap on and less intensive PNS therapy may be delivered with the EEG cap off.

The training/feedback "game" is modulated based on performance both in real time and over subsequent sessions. The algorithm may reside in the app on phone/tablet or a standalone computer or in conjunction with cloud processing. For cloud processing, data from phone/tablet is uploaded to cloud where it is analyzed and next cycle the updated algorithm is sent to phone/tablet. The algorithm constantly improves or learns based on data collected from other patients as well as evolution of the PNS therapy parameters, EEG or other training feedback parameters of the current patient.

Specific treatment algorithms include: 1) For Single SES treatments: a) SES alone—no EEG diagnostic or feedback; b) SES with EEG monitoring and closed loop feedback for stimulation; c) Single and dual limb treatments. 2) For combination treatments: a) SES+EEG closed loop feedback+dexterity training; b) SES+EEG closed loop feedback+dexterity training+haptic feedback; c) SES+dexterity training; d) SES+monitoring of spontaneous actions (i.e. during routine non-task activities).

For the conditions listed in FIGS. 10-14, a range of stimulation parameters are used. A key goal of the paradigm is the use of a feedback system to titrate parameters to each individual. Thus, the range of parameter sweeps to be tested are outlined in order to arrive at the customized range. A variety of machine learning and statistical techniques are used to customize parameters. For example, use linear methods such as multivariate regression models are used to quantify the relationship between a feedback parameter and the stimulation set. Non-linear methods such as neural networks are also used.

Figures 15B, 15C:
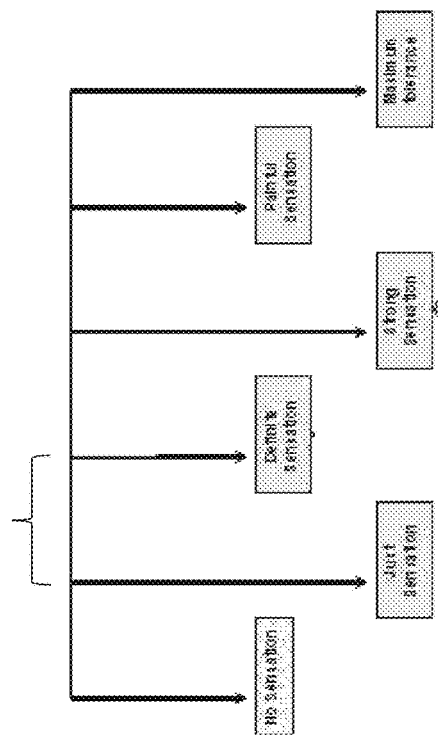
FIG. 15B shows examples of sensory fiber types and properties that may be used to differentially modulate peripheral nerves. In general, modulation of stimulation parameters may be titrated to optimize stimulation of sensory fibers. Mixed sensorimotor nerves are known to contain multiple nerve fibers with varying roles; the table in FIG. 15B shows a typical mix of fibers. They are also known to have different excitability; the methods and apparatuses described herein may change stimulation parameters in order to maximize cortical modulation. Cortical modulation may be assessed using resting-state EEG, evoked EEG responses, and motor task parameters as described herein.
FIG. 15C illustrates an increasing sensitivity of a user's perception of stimulation. The apparatuses and methods described herein may provide SES that targets A(beta, gamma) fibers. One parameter to selectively activate sensory nerves may be the amplitude of the current; this is shown in FIG. 15C. An exemplary protocol may titrate the stimulation parameters between "definite sensation" down to below "just sensation" (bracketed region). For example, an apparatus as described herein may automatically determine this stimulation range based on subjective feedback from the user. Concurrently or subsequently, parameters such as intensity, frequency, pulse duration as well as burst mode parameters may be varied.

In regard to the specific stimulation parameters, a stimulation frequency is used that ranges from 0.001 to 1000 Hz. This in inclusive of all sub frequencies (e.g., 10, 10.1, . . . 10.9,11). The stimuli may adapt parameters with a block design (e.g., stimulation of a frequency "sweep" starting at 5 Hz and ending at 20 Hz; another example is a burst mode where two separate fixed bursts are employed). Waveform shapes may or may not be charge balanced—including a biphasic square wave pulse. The waveform of the stimulation could also be varied to include any arbitrary waveform shape (e.g. saw tooth, sinusoid, white noise, ramp, multiple state pulses, triangle). Waveform duration may vary from 1-500 microsec; the specific range is limited by the chosen frequency. The duty cycle of the stimulation may be varied from 0 to 100%. The intensity will also be controlled; it can range from 0 to >100 mA. A variety of stimulation durations ranging from 1 minute in duration to continuous (always on) may find use. Additional stimulation parameters are shown on FIG. 15A. The adaptive algorithm determines the specific duration of stimulation for each individual. For multiple nerve stimulations (e.g., median, ulnar, radial), all nerves may be stimulated simultaneously or may be stimulated using a patterned train (e.g. sequential or any combination with variable temporal lags).

Various parameters influence the development of an efficacious stimulation or treatment algorithm that may be personalized to individual need and performance. Parameters of interest include the frequency of stimulation, duty cycle (duration of the on/off signal times), waveform shape (e.g. biphasic, monophasic, sinusoid, saw-tooth), duration of stimulation in a single session, number of such stimulation sessions per day, week or month, the nerves that are stimulated, electrodes location relative to the nerves and the ability of the algorithm to adapt to patient-specific responses to stimulation. Adaptive algorithms have the ability to monitor feedback or outcomes and up/down titrate or modulate the response to achieve desired treatment or performance.

Assessments of the outcome of stimulation may depend on the following parameters: behavioral metrics (like reaction time etc.), neurophysiological biomarkers, and subjective assessments of response from each individual. For the upper limb, behavioral metrics will rely on changes in kinematic (e.g., movement characteristics) and kinetic (e.g. force) parameters. Metrics may also include objective and subjective parameters or a combination of both. These include the speed of movements, accuracy of movements in response to visual or other cues, accuracy of performance of a motor task, and spontaneous movements that are not directly related to a task. Parameters that involve both the distal and the proximal limb may be assessed. This could include, for example, assessment of finger movements and individuation to hand grip measurements to movements of the arm itself. This might also include measurement of forces using electronic dynamometers either embedded in the stimulation device itself or an attachment for the phone. Coordination of these movements may also be used to measure performance. For the lower limb, similar metrics are used. This may include gait parameters such as stride length, step length, base of stance, speed of movement and variability of steps. In addition, response time to external stimuli may be improved by SES. Speed of foot tapping as a measure of lower extremity function may be assessed. For oromotor function, vocalization and ability to swallow may be assessed. For pain conditions, self assessment of pain by the user may be used. For erectile dysfunction, ability to initiate or maintain an erection may be assessed by self report, etc.

A variety of measurements may be used to monitor movement parameters. For example, a phone app may allow individuals to perform a visually guided finger dexterity task to measure speed and accuracy. An accelerometer and gyroscope in the phone may monitor speed, accuracy and trajectory of limb movements during the treatment period. In this case, the subject would make movements while holding the phone. Accelerometers, magnetometers and gyroscopes that are embedded in the stimulation device to monitor limb movements may also find use. Video on the phone itself may be used; the app would then automatically segment the images and determine movement parameters. For the lower limb, one can envision a similar combination of direct app based measurements (e.g., tapping on the phone screen with the foot), the use of accelerometer/magnetometer/gyroscopes and the use of sensors built into the stimulation device itself. In some embodiments, the user's voice or other sound may be used to monitor treatment progress. Additional outcome measures are listed in FIG. 16.

EEG recordings before/during/after stimulation are used to assess response to PNS. EEG requires placement of electrodes, as exemplified by the 10-20 electrode system designed in the form of a head cap in FIG. 2. A reference electrode is then typically placed near the ear or the mastoid process. Active recording electrodes are placed on the scalp; these will be placed either using a conductive gel or as dry electrodes. Each cortical electrode is referenced with the ear reference. In the case of significant artifacts, cortical EEG electrodes will be analyzed in a differential mode (i.e., each electrode will be referenced to the ear and then to each other); this will allow optimal common-mode rejection. Time-frequency spectral analysis may be used to determine the power in each frequency band (i.e., 0-55 Hz).

Clinical experiments were conducted using this system. A relative decrease in ipsilesional resting state low frequency power was observed primarily in the delta band (0-4 Hz) and theta band (4-7 Hz) immediately after PNS when compared to the baseline resting period, as shown in FIG. 17. Secondarily, a decrease in ipsilesional motor theta and alpha power (8-12 Hz) were significantly correlated with fractionation changes with SES. Together, the results highlight the importance of low-frequency, ipsilesional cortical oscillations in association with behavioral changes in response to SES. The low frequency oscillatory power loss could also signify cortical plasticity wherein the underlying cortical networks transition from an idling state to motor-function related recruitment.

Example 1: Treating Stroke Patients with SES

Eight participants with a history of acquired brain injury and distal upper limb motor impairments received a single two-hour session of SES using transcutaneous electrical nerve stimulation. Pre- and post-intervention assessments consisted of the Action Research Arm Test (ARAT), finger fractionation, pinch force, and the modified Ashworth scale (MAS), along with resting-state EEG monitoring.

The primary outcome measurements consisted of the standardized ARAT and kinematic measurement of finger individuation, as measured by the finger coupling index (FCI). ARAT has been validated to measure defined domains of distal hand function (i.e. proximal, grasp, grip, and pinch tasks). Digital video recordings were obtained for kinematic motion analysis using a 30 Hz video capture system and were analyzed using a custom Matlab script to record beginning position and end position of the required task. FCI measurements were obtained by asking the participant to begin in fully extended digit position, or as near as possible, then while maintaining this position flex only the middle finger and then analyzed using a custom Matlab script. FCI was then calculated as the angle traversed by the passive middle finger divided by the angle traversed by the active index finger (FIG. 18). Three trials were averaged to obtain the mean FCI. Secondary outcome measurements included finger pinch force (standardized dynamometer), and MAS to assess spasticity affecting wrist and finger flexion and extension. Outcome assessments were measured immediately before and after the intervention. Resting state EEG data with eyes open was acquired (Enobio, Neuroelectrics Corp.) for a duration of 10 minutes before and after stimulation, using 8 electrodes over the Fp1, Fp2, C3, C4, P3, P4, O1, O2, 10-20 system EEG positions at 500 Hz with a mastoid reference.

Results of kinematic and clinical outcome measurements are presented in FIG. 19. Mean scores were significantly improved after PNS including ARAT total score, overall ARAT completion time, ARAT pinch tasks subset completion time, FCI, and MAS. The mean change in ARAT score was 1.56 points change (or 3.7% improvement) after one session of SES (p<0.05). ARAT domain subsets were further analyzed to determine whether one specific domain improved or a generalized effect in distal upper limb function could be observed. Significant improvement was noted for speed (overall time to complete all tasks decreased by 1.6 seconds (13.8% change; p<0.05) and pinch tasks time which reduced by 6.6 seconds (29% change; p<0.05). Changes in proximal tasks time, grasp tasks time, and grip tasks time were not significant. Finger fractionation significantly improved; FCI decreased from 0.68 to 0.53 (22% change). Of the secondary outcome measurements, MAS decreased significantly by 2.25 points (60% change) amongst those who had baseline spasticity (p<0.05), while mean pinch force increased by 1 pound (9% change). Although the latter did not reach statistical significance, a trend toward improvement was noted (p=0.14).

Figure 20:
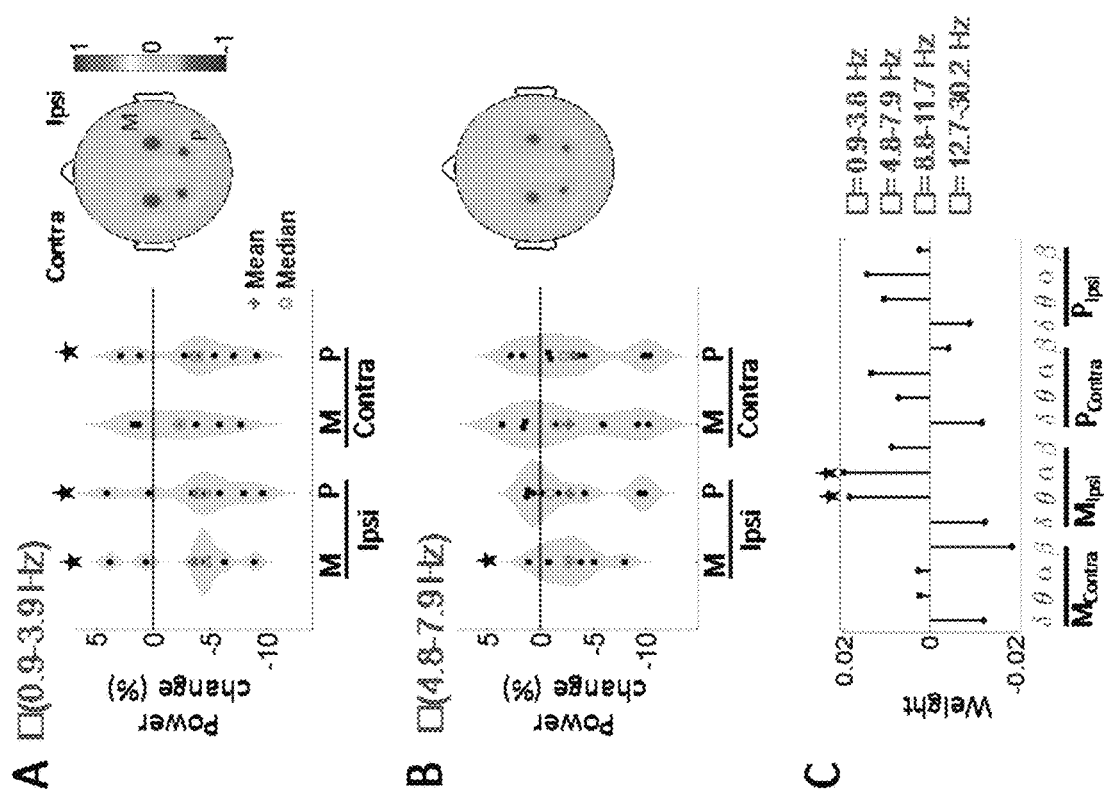
FIGS. 20A-20C shows changes in resting state EEG power across the subjects in a clinical study.

FIG. 20 shows the distribution of percentage change in mean resting state EEG power across the eight subjects, pre to post intervention, within the delta frequency band and theta frequency band with head plots depicting 1/coefficient of variation (mean/standard deviation) of group level percentage changes. The star sign represents a significant change in group level resting state EEG power from zero. FIG. 20A shows the magnitude of the coefficients of the multivariate robust ridge model from regressing mean FCI changes to mean power changes, pre to post intervention, with the star sign depicting coefficients whose absolute magnitude were greater than 95% of those produced by random data permutation.

SES caused a significant decrease primarily in mean ipsilesional resting state parietomotor EEG power, especially at low frequencies (delta 0.9-3.9 Hz and theta 4.8-7.9 Hz bands, p<0.05, Bonferroni corrected, FIG. 20A-B). In contrast, no significant changes were found for alpha and beta frequencies (8.8-11.7 Hz). In addition, combined theta and alpha power changes over the ipsilesional motor cortex were significantly correlated with fractionation changes (p<0.05) when controlling for all other predictors in the multivariate ridge model (FIG. 20C), with a ridge parameter value of 12.13 computed by cross-validation. It should be noted that ridge regression shares coefficient values amongst correlated predictors while shrinking coefficients of predictors not correlated with the response variable. The study showed positive effects of SES on finger individuation and identified cortical oscillations that may be important electrophysiological biomarkers of individual responsiveness to SES. These biomarkers are targets to customize SES parameters to individuals with distal hand deficits.

Based on the results outlined above, one embodiment of the device would aim to "self-titrate" the SES parameters (e.g., but limited to amplitude, frequency, duty-cycle, burst mode duration) based on monitoring of the EEG signal. More specifically, the raw/referenced EEG signal would be band-pass filtered into multiple frequency bands (e.g. 0-4, 4-7, 8-12, 13-20, 21-40, 40-200; any combination and step size may be chosen). For a specific embodiment based on theta and delta waves, the device would calculate the power in those bands (e.g. using time-frequency analysis vs RMS vs Hilbert transform or other). The device would establish a baseline value prior to stimulation and then monitor the amplitude in a continuous manner. The device would be able to stop stimulation for assessments if there is a large stimulus artifact. Stimulation would stop or change if no decrease in power is detected over time. The device would then be capable of choosing another set of parameters for subsequent testing.

In addition to "resting-state" EEG measurements listed above, evoked potential analysis may be used to titrate the dose. In this case, the EEG signal or the evoked neurophysiological signal (i.e. from the scalp/neck/face/shoulder/arm or other site) would be measured for each stimulation pulse. The device would create an average response based on a moving average of the recorded signals. The system would also titrate parameters based on this averaged evoked response.

Example 2: Combination Therapy: Treating Stroke Patients with SES+FDT/Haptics

Building on the above study in Example 1, the synergistic effects of combination of therapies for hand rehabilitation were tested in the same subject. A motion sensor dataglove, real-time vibrotactile/haptic feedback and SES of peripheral nerves in the affected hand were combined and the changes in motor function and hand/finger movement were measured. The study assessed if a multimodal approach to hand rehabilitation could improve hand and finger function in subjects with chronic motor disability after stroke. Two important goals were to use state-of-the-art technology to provide real-time feedback during rehabilitation as well as to fully elucidate the patient characteristics that predicted improvement for each modality.

Figure 21:
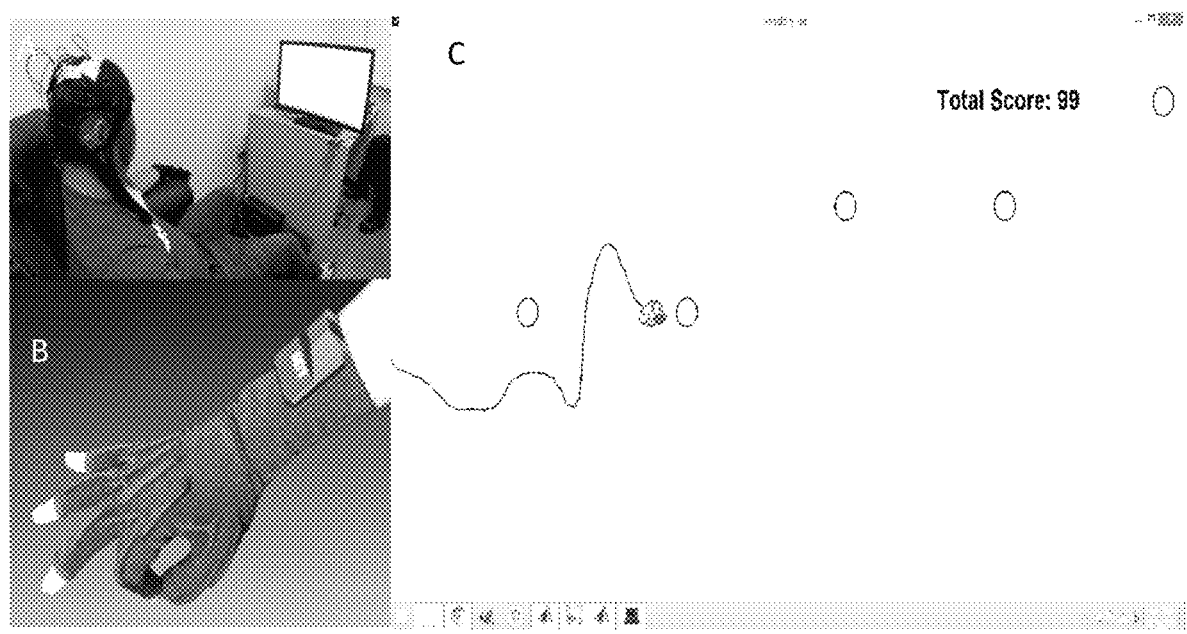
FIGS. 21A-21C shows an example of game based training setup, glove, and video training/testing, respectively.

The following were tested: (1) sub-motor/supra-sensory electrical stimulation of the ulnar/radial/median nerve at the wrist; (2) game-based rehabilitation of hand and finger function using a 'sensored dataglove' that could monitor finger movements, or finger dexterity training (FDT); and (3) the incorporation of vibrotactile haptic (haptic feedback) cues to provide error signals during the game-based rehabilitation. As shown below in FIG. 21, the game relied on finger movements to move the central character. The subject engaged in a finger rehabilitation game that used the glove to monitor finger kinematics in real-time. Primary outcome measures were detailed kinematic parameters (FCI, active range of finger motion) and gross measures of hand function (ARAT, and nine-hole peg test, NHPT). Secondary outcome measures of spasticity were pinch force and MAS.

Results of the gross effects of two-hours of peripheral nerve stimulation of the radial, ulnar and median nerves (2 hours, 1 Hz trains, single pulses at 10 Hz over 500 ms, 50% duty cycle, 1 ms pulse width) are shown in FIG. 22 A, B. Specifically, there was a significant reduction in spasticity or MAS and significant improvement in ARAT total score.

In contrast, there were more mixed effects on the finger kinematics. As shown in the FIG. 22C, there was no significant change (i.e. at the population level) in the finger-coupling index after SES stimulation. Finger coupling index is plotted as the finger coupling ratio (FCR), which is a measure of the ability to independently move two fingers (i.e. a value of 1 indicates lack of individuation and completing coupling; a value of 0 indicates perfect individuation). The graph indicates that after training there was no significant improvement in FCR, or the individual's ability to fractionate. Similar scores from 'pre' to 'post T0' were observed.

Figure 22A:
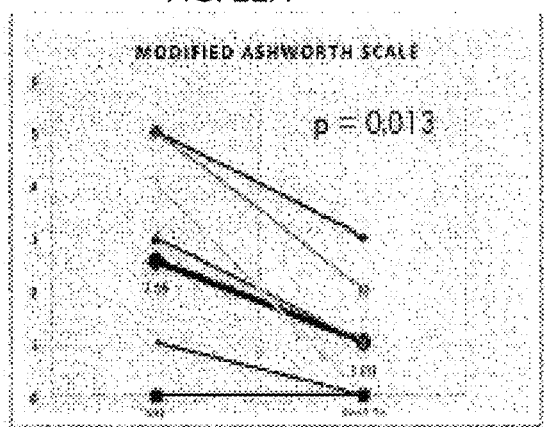
FIGS. 22A-22D show the results of PNS in a clinical study of stroke patients. Specifically, the figures show a change in MAS (FIG. 22A), eARAT (FIG. 22B) and FCR after SES (FIG. 22C), and FCR after SES+haptic feedback (FIG. 22D).
Figure 22B:
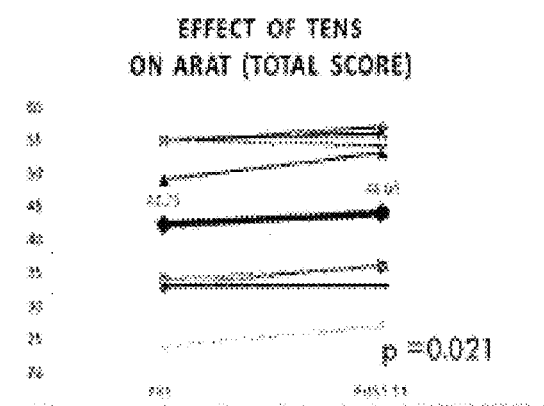
Figure 22C:
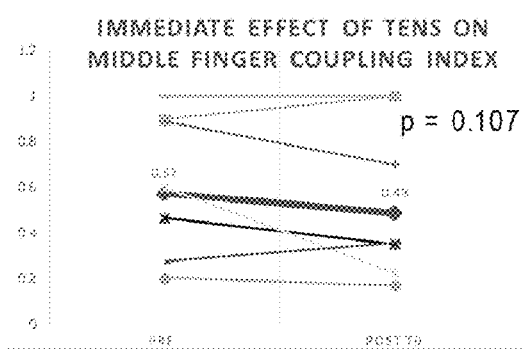
Figure 22D:
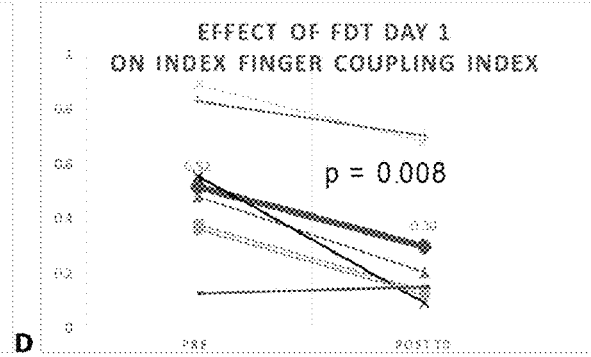

FIG. 22D shows the effects of finger dexterity training (FDT) using the adaptive gaming (or rehabilitation) program described above on finger kinematics, measured using FCR. The game tracked the subject's finger kinematics, or the middle finger and the index finger joint angle at the 'knuckle' finger, using the sensored dataglove that could monitor hand and finger motion. The subjects were required to increase individuation over time to succeed in the game. FCR was measured before and after training. Each session typically lasted 1 hour, during which the subject's performance was monitored and the degree of difficulty was adjusted based on the level of performance. Results show that there was a significant improvement in the ability to fractionate (i.e. a reduction of the finger coupling scores from 'pre' to 'post T0') after combination treatment of SES+haptic feedback or finger dexterity training.

Figure 23:
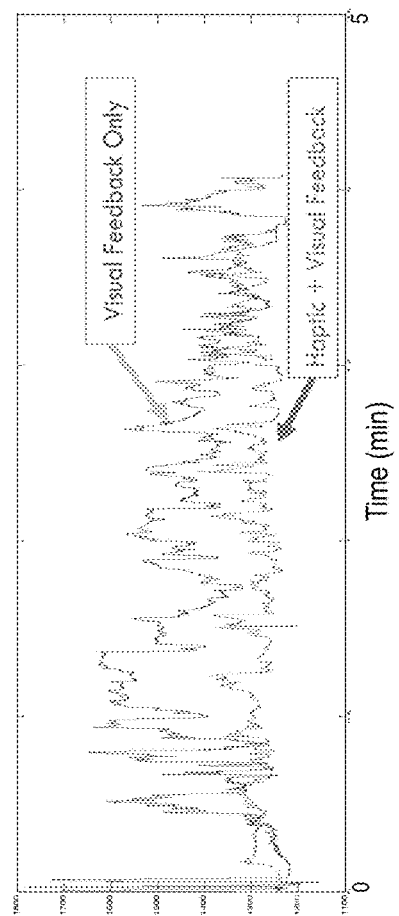
FIG. 23 illustrates the improvement in finger movement using haptics as part of game based training. The effect of combination treatments on finger movement (traces of individuation) with SES+visual (top "visual feedback only") vs. SES+visual+haptic feedback (bottom "haptic+visual feedback").

Effects of adding vibrotactile haptic feedback of errors during the training were also tested. In three subjects there was a significant improvement from adding the haptic feedback, as shown for one subject in FIG. 23. Individuation improved during game play with the additional haptic feedback as noted by the significant reduction in the errors. The traces below illustrate movements of the finger that should have kept still during the training. With haptics, as shown by the red trace, there was greater ability to keep the finger still.

The results show that while neuromodulation using PNS was broadly effective on gross measures of hand function (i.e. reduced spasticity, allowed increased force), it was less effective on finger kinematics. An opposite pattern was apparent with finger-based training. Haptics-based approach appeared to improve finger kinematics over visual-based regular training. These results provide important proof and validate the principle of the combined benefits of neuromodulation using PNS/SES as well as the use of a dataglove with haptic feedback. The effects of each can be non-overlapping and indicate that combination in a single product would be ideal. Importantly, the feasibility/basis/rationale of a model for optimal strategies to combine modalities to improve hand and finger function after stroke and other neurological conditions that limit limb movement was demonstrated.

Example 3: Treatment of Impotence Using SES

Figure 24:
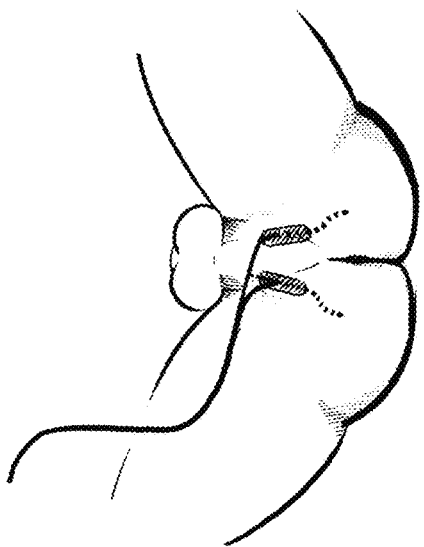
FIG. 24 shows the use of PNS to stimulate the perineum.

One embodiment of the technology is for the treatment of impotence using SES Stimulation: In this case, the patient or healthcare provider applies and electrode to perineum. There may be positive and negative electrodes for each pudendal nerve, integrated into either one patch or component for each nerve or one patch or component for the whole perineum as shown in FIG. 24. The user may need to trim hair prior to application of the electrode or patch. If the electrode has a wire, then it should be plugged into the control module. In other embodiments, the electrode communicates wirelessly with the control module. The user may then put on an EEG in the shape of a headband and then opens an app on his phone. The app has previously uploaded data from last stimulation session and last training session. The server has revised the stimulation algorithm and pushed it back down to the app. The user then starts his stimulation session. The phone then communicates using Bluetooth low energy with the EEG monitor and the electrode control module. Stimulation signals are sent to the control module while EEG data is received from the EEG monitor. The EEG data is used to modulate the stimulation in real time according to algorithm. Analysis of the EEG data allows the phone to prompt the patient to adjust the EEG sensor if not positioned properly. The user then removes and unplugs electrode and may throw it away or it may be reused. He then may charge the control module using microUSB charger and recharge EEG monitor using the micro USB charger. In the background, phone uploads newest stimulation data to cloud server.

Training: The patient applies monitoring device (circumferential ring or adhesive patch) on the penis (FIG. 25.) He starts the app on his phone and begins the erotic stimulation method of personal choice. The monitoring device monitors either blood flow or penile elongation and transmits data back to phone as shown in FIG. 26A, B. The phone provides feedback (i.e., biofeedback functionality). The patient removes and either disposes of or cleans monitoring device. The phone transmits data back to the cloud server for analysis and to updates the algorithm for the next stimulation session. The user plugs the device or transmitter in to charge via microUSB.

Example 4: Gaming (or Other Hand Performance Improvement)

Visuomotor coordination, manual dexterity, and finger individuation are key to playing video games, whether it is based on a regular gaming consul or a phone/tablet. PNS is known to change the motor representation of limb movements in healthy subjects. Importantly, there is literature that suggests that PNS may help with perceptual skills and manual dexterity. One embodiment of the device is designed to enhance gaming skills designed to improve visuomotor coordination, manual dexterity, and finger individuation, reflexes, precision movements, speed (of tapping, etc.), smoothness of finger movement and hand-eye coordination.

One specific embodiment includes the following elements: (1) a wrist-worn device that is able to variably modulate the radial, ulnar, and the median nerves, (2) wireless connectivity to a mobile phone and/or the specific gaming console, (3) a device and/or method to quantitatively monitor visuomotor coordination, manual dexterity, and finger individuation, (4) an algorithm to adapt parameters of stimulation (e.g., nerves, frequency, amplitude, waveform, duty cycles) to personalize the enhancement of performance. In one embodiment, the wrist-worn device would be able to couple with finger sensors (e.g. caps attached to the fingertip, or a partial glove; or sensor rings worn on fingers) in order to directly monitor kinematic improvements. In another embodiment, a mobile phone application would be designed to measure performance using a range of metrics (e.g. reaction time, sequence learning, individuation). The application then quantifies performance metrics and then adapts performance in closed-loop manner. A mobile camera system to monitor hand and finger movements may be used in order to quantify movements, motor function and response times.

Stimulation: The patient applies the stimulation device to wrist and puts on the headband EEG. She then opens an app on the phone which has previously uploaded data from last stimulation session and last training session. The server has revised the stimulation algorithm and pushed it back down to the app. She then starts a monitored stimulation session. The phone communicates using Bluetooth low energy with the EEG monitor and the electrode control module. Stimulation signals are sent to the control module while EEG data is received from the EEG monitor. The EEG data is used to modulate the stimulation in real time according to algorithm. Analysis of the EEG data allows the phone to prompt the patient to adjust the EEG sensor if not positioned properly. At the completion of the stimulation session, the user takes off the EEG monitor and plugs in with USB charger. She leaves the wrist unit on to continue with sub-sensory or minimally sensory stimulation. The phone either continues to control stimulation or pushes optimized program to stimulation device. The user goes about their life (work, sleep, TV watching) with unmonitored stimulation. The phone prompts the user that stimulation is complete. User takes off device and plugs in to recharge. A similar leg bracelet (anklet) stimulation device or a stimulator in a shoe or detachable shoe sole/insert could be placed on the lower limbs and coupled with an EEG feedback monitor to provide optimal stimulation and achieve the desired functional performance.

Training: The patient opens the app on phone or tablet. She plays series of games which test and train various fine motor skills. The app dynamically adjusts difficulty of different aspects of the game to keep user at the edge of their capacity. Skills trained include speed of tapping, finger individuation, response time to visual, sound, or vibratory stimuli, precision of movement, smoothness of movement, and hand-eye coordination. Additional auditory, vibration, or visual cues are provided to either assist or confound user. (e.g., in a maze game, background may flash right before the target changes direction.) The phone transmits data back to cloud server for analysis and to update algorithms.

In some variations, a portion of the apparatus may include a video game controller or console. For example, the video game console (or an adjunct device that connects to the console) may be configured to execute the control logic (e.g., software, firmware, etc. including a non-transitory computer-readable storage media containing a program that controls all or a portion of the apparatus).

A gaming apparatus may be configured for enhancing performance on manual tasks involving finger individuation by closed-loop electrical stimulation. The stimulator may be adapted to be worn on user's arm, hand or arm and hand (e.g., as a bracelet, bracer, wristlet, watch, glove, etc.) and may include one or more electrodes, a power source, a controller, etc., wherein the stimulator is configured to deliver an electrical stimulation from the electrodes to one or more of the user's radial, ulnar and median nerves when worn. The stimulator may be adapted to be worn on the user's leg (e.g., as an anklet, sole/insert or a smart sock, etc.) and may include one or more electrodes to deliver electrical stimulation to the tibial/leg nerves to improve performance. In this case, the performance may enhance leg-eye coordination while playing video games using a foot controller (race-car driving such as Grand Turismo) or race-car driving on motor speedways.

As mentioned, the apparatus may include a non-transitory computer-readable storage medium storing a program thereon, wherein the program causes a processor such as the gaming system to: present a manual training task involving finger individuation (such as a video game). The game console may include a controller. The program may analyze the subject inputs from the subject's fingers (including thumbs, or legs) onto the game controller (e.g., button pushes, etc.), and may also receive input on accuracy from the console, and may use this information to estimate a performance metric based on the finger individuation. Based on this information the software may adjust the electrical stimulation and may transmit the adjusted stimulation parameters to the stimulator.

For example, a video game console itself may be a master controller (e.g., may run the program/control logic) over the apparatus. The apparatus may titrate SES onset and titrate SES parameters based on performance metrics. In this scenario, a wrist band stimulation unit may be charged by (i.e. in between sessions) and wirelessly connected to the video game console itself, or to an apparatus connected to the console. SES could be turned on the console itself or via software controls built into the console. Titration of SES parameters may be performed via performance metrics measured via the video game controller unit. For example, in an X-Box™ type controller, the speed of button pressing and multi-finger coordination would be continuously monitored and used to titrate the SES parameters. Similarly or additionally, performance on the video game itself could be used to titrate the SES parameters. Parameters that could be modified include, but are not limited to, the amplitude of the current (e.g. % below sensory evoked threshold), the frequency of stimulation (e.g. between 6-20 Hz), and the number and type of nerve stimulated (e.g. median vs median+ulnar vs median+ulnar+radial).

The apparatus may be purchased separate from the video game console system, or it may be included (and packaged) with the system. For example, the apparatus may include a video game (that is played on gaming console, such as an Xbox™ or PlayStation™) and a stimulator (e.g., configured as a wrist band). A game for training and/or assaying performance of the apparatus (e.g., to assess how the player is responding to ongoing stimulation) could be created and/or configured for operation with the gaming system. As mentioned, it may assess finger tapping, reaction time, multi finger coordination and other parameters as described above.

The game/console may keep track of the stimulation protocol (and there may be a plurality of different stimulation protocols, e.g., between 10 and 1000, between 20 and 500, between 30 and 200, more than 500, more than 1000, etc.). Various stimulation protocols may be associated with the particular user or generally to multiple users and associated with improvements in performance in general or in a particular game/training. For example, a subject (user) may select one or more stimulation protocols that led to the most improvement in this game or the apparatus may automatically optimize by changing the protocols to determine which result in improvements.

For example, a subject may use the apparatus for 30 days in a row, and the subject and/or the apparatus (automatically) may determine that a particular protocol or protocols (e.g., stimulation parameter protocols 23 and 68) result in improved parameters x and y the most. The apparatus may generate recommendations of which protocols may help each game the most based on the manual skills applied in a particular game. For example, a game requiring repetitive tapping may it may benefit a typical or specific user to use protocol 24 versus other types of games (e.g., a "shooter" games), which may benefit most from another protocol or class of protocols (e.g., protocol 56). Some protocols may differentially apply electrical stimulation to different nerves (e.g., radial, ulnar and median nerves). In some variations, a user may self-program the stimulation wrist band using buttons to get to the right number.

Example 5: Memory/Training/Sleep

Modulation of neural processing during sleep is known to enhance declarative memory and motor memory. Importantly, it is also known to provide insight (e.g. discover hidden rules in seemingly unrelated data points) into complex problems. All of these processes are critical to our daily lives, whether is learning new motor skills, enhancing our perceptual skills, learning new facts and knowledge, and gaining insight into challenging problem. The devices described previously can be used to modulate these processes and thus boost all elements of sleep dependent processing.

A specific embodiment of the device that will facilitate this includes the following elements. (1) a wrist-worn device that can stimulate radial/ulnar/median nerves, (2) an accelerometer in the device that will be used to detect sleep stages, (3) an algorithm to stimulate only during particular sleep stages (e.g., NREM 1-IV, REM). This system would be worn during the night and provide specific PNS stimulation during phases of sleep. The system can either during entire phases of sleep (e.g., during NREM sleep, during REM sleep or particular features of sleep such as spindles/slow oscillations, etc.). In another embodiment, an EEG cap or a partial EEG system would be used to detect sleep stages and particular sleep features (e.g. slow oscillations, spindles, delta wave sleep, REM).

In another embodiment, there are one or more pairs of electrodes that can be controlled using a mobile application that can be placed in any region for a similar patterned stimulation. For example, it is known that the trigeminal nerve may modulate facial motor areas and areas that may be important for speech/language processing. In this embodiment, electrodes are placed on the face in the sensory areas associated with the trigeminal nerve. Sensors on these adhesive electrodes are able to detect sleep stages using accelerometers and/or EMG electrodes.

Although various illustrative embodiments are described above, any of a number of changes may be made to various embodiments without departing from the scope of the invention as described by the claims. As one example, any and all devices and systems may have removable electrodes placed in proximity to nerves. In other embodiments, devices and systems may have electrodes that are implantable (under the skin) on or around nerves of nerve bundles. These implantable electrodes may be in many configurations including but not limited to linear, cuff or ring electrodes, coil or microneedles. These electrodes may be connected to an external generator or an implantable device that sends electrical pulses to peripheral nerves. Any component, device and system described herein can therefore be used in combination with any disease or condition described herein through the stimulation of any of the nerves listed using any and all stimulation parameters listed.

The order in which various described method steps are performed may often be changed in alternative embodiments, and in other alternative embodiments one or more method steps may be skipped altogether. Optional features of various device, sensor, stimulation algorithm and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of improving hand motor nerve function of a subject recovering from a stroke by closed-loop control of applied stimulation, the method comprising:
    applying a transdermal electrical stimulation to one or more of the subject's radial, ulnar and median nerves;
    measuring an electroencephalogram (EEG) from the subject;
    determining an indicator of low-frequency cortical oscillations from a change in power of a delta or a theta wave portion of the EEG;
    adjusting the transdermal electrical stimulation based on the indicator; and
    repeating the steps of applying, measuring, determining and adjusting.

2. The method of claim 1, further comprising placing a wearable transdermal stimulator onto one or more of the subject's arm and hand.

3. The method of claim 1, further comprising performing a training task involving activation of one or more of the subject's radial, ulnar and median nerves.

4. The method of claim 1, wherein adjusting the transdermal electrical stimulation comprises adjusting one or more of: intensity, current amplitude, frequency, duration, duty cycle, times/day, pulse duration, burst frequency, burst duration, or total treatment period.

5. The method of claim 1, further comprising maintaining the stimulation intensity as sub-sensory or nearly sub-sensory based on subject feedback.

6. The method of claim 1, wherein determining the indicator of low-frequency cortical oscillations comprises determining the indicator in a resting state.

7. A method of improving a subject's performance on manual tasks involving finger individuation, the method comprising:
    applying a transdermal electrical stimulation to one or more of the subject's radial, ulnar and median nerves;
    performing a manual training task involving finger individuation and estimating a performance metric based on the finger individuation wherein the performance metric is correlated with low-frequency cortical oscillations;
measuring an electroencephalogram (EEG) from the subject comprising measuring a change in delta or theta wave portion of the EEG;
adjusting the transdermal electrical stimulation based on the measured EEG and the performance metric; and
repeating the steps of applying performing and adjusting over a plurality of days.

* * * * *